United States Patent
Petit, II et al.

(10) Patent No.: US 7,041,651 B2
(45) Date of Patent: May 9, 2006

(54) CELLULAR UPTAKE OF BIOACTIVE AGENTS

(75) Inventors: Robert G. Petit, II, Newtown, PA (US); Edward C. Shinal, Pennington, NJ (US)

(73) Assignee: Aesgen, Inc., Princeton, NJ (US)

( * ) Notice: Subject to any disclaimer, the term of this patent is extended or adjusted under 35 U.S.C. 154(b) by 96 days.

(21) Appl. No.: 10/796,261

(22) Filed: Mar. 9, 2004

(65) Prior Publication Data

US 2004/0176319 A1 Sep. 9, 2004

Related U.S. Application Data

(60) Division of application No. 09/993,465, filed on Nov. 14, 2001, now Pat. No. 6,734,170, which is a continuation of application No. PCT/US00/13260, filed on May 15, 2000.

(60) Provisional application No. 60/134,442, filed on May 17, 1999.

(51) Int. Cl.
*A61K 31/70* (2006.01)
*C07C 229/00* (2006.01)

(52) U.S. Cl. .................... 514/23; 514/53; 514/54; 536/123.1; 536/123.12; 536/123.13; 562/563

(58) Field of Classification Search .......... 514/23, 514/53, 54; 536/123.1, 123.12, 123.13; 562/563
See application file for complete search history.

(56) References Cited

U.S. PATENT DOCUMENTS

| 4,849,408 | A |   | 7/1989  | Sommermeyer et al. ...... 514/18 |
| 4,983,595 | A |   | 1/1991  | Benjamin et al. ............ 514/174 |
| 5,397,803 | A |   | 3/1995  | Smith et al. ................. 514/563 |
| 5,438,042 | A | * | 8/1995  | Schmidl et al. ................ 514/21 |
| 5,438,075 | A | * | 8/1995  | Skubitz et al. ............... 514/563 |
| 5,545,668 | A |   | 8/1996  | Skubitz et al. ............... 514/561 |
| 5,607,975 | A |   | 3/1997  | Smith et al. ................. 514/563 |
| 5,684,045 | A |   | 11/1997 | Smith et al. ................. 514/563 |
| 5,726,146 | A |   | 3/1998  | Almada et al. ................. 514/2 |
| 5,744,166 | A |   | 4/1998  | Illum ......................... 424/501 |
| 5,763,485 | A |   | 6/1998  | Smith et al. ................. 514/463 |
| 5,792,753 | A |   | 8/1998  | Falk et al. ...................... 15/54 |
| 5,849,335 | A |   | 12/1998 | Ballevre et al. ............. 424/535 |
| 5,891,467 | A |   | 4/1999  | Willis .......................... 424/450 |
| 5,985,850 | A |   | 11/1999 | Falk et al. ..................... 514/54 |

FOREIGN PATENT DOCUMENTS

| EP | 0614659    | 3/1994  |
| EP | 0845265    | 8/1996  |
| EP | 0873749    | 10/1998 |
| WO | WO-97/14310 | 4/1997 |

OTHER PUBLICATIONS

Culliford, S. J., et al., "Activation of a Novel Organic Solute Transpoeter in Mammalian Red Blood Cells," *J. Physiol*, 489, University Laboratory of Physiology,(1995), 755-65.

Steenge, G. R., et al., "Stimulatory Effect of Insulin on Creatine Accumulation in Human Skeletal Muscle," *American Journal of Physiology*, 275, (Dec. 1998), E974-E979.

* cited by examiner

*Primary Examiner*—Elvis O. Price
*Assistant Examiner*—Michael C. Henry
(74) *Attorney, Agent, or Firm*—Schwegman, Lundberg, Woessner & Kluth, P.A.

(57) ABSTRACT

Provided is a composition and a method for increasing cellular uptake of bioactive agents, particularly those compounds termed "small molecules" into the cells of mammalian tissue, such as the epithelial cells of the mucosa.

11 Claims, 13 Drawing Sheets

RELATIVE L-GLUTAMINE UPTAKE INTO CELL MONOLAYER FROM VEHICLE vs NON-VEHICLE

RELATIVE L-ASPARAGINE UPTAKE INTO CELL MONOLAYER FROM VEHICLE vs NON-VEHICLE

RELATIVE ACYCLOVIR UPTAKE INTO CELL MONOLAYER FROM VEHICLE vs NON-VEHICLE

RELATIVE L-GLUTAMINE UPTAKE INTO CELL MONOLAYER FROM VEHICLE vs NON-VEHICLE

CELLULAR UPTAKE OF BIOACTIVE AGENTS

RELATED APPLICATIONS

This application is a divisional of U.S. patent application Ser. No. 09/993,465, filed Nov. 14, 2001, Now U.S. Pat. No. 6,734,170 which is a continuation under 37 CFR § 1.53(b) of PCT Application Ser. No. PCT/US00/13260, filed May 15, 2000 and published as WO 00/69470 on Nov. 23, 2000, which claimed priority from provisional U.S. Patent Application No. 60/134,442, filed May 17, 1999, which applications and publications are incorporated herein by reference.

BACKGROUND OF THE INVENTION

Absorption of biomolecules, such as amino acids and proteins, is critical to cellular function. About 75 percent of the solids in the mammalian body are proteins, including enzymes, polypeptides such as cytokines, nucleoproteins, transport proteins, and structural proteins. The principal functional constituents of these proteins, amino acids, polypeptides and isolated amino acids, are also important for cellular metabolic functions. The amino acid glutamine, for example, serves important functions in metabolism, including transport of carbon and nitrogen between tissues. It is a precursor for hepatic and renal gluconeogenesis, as well as urea synthesis in the liver and ammonia production in the kidney. A number of cell types, particularly the cells of the intestinal mucosa, also utilize large amounts of glutamine as their major source of respiratory fuel.

The effectiveness of amino acid supplementation for treatment of a variety of physiologic disorders has been demonstrated. D-serine supplementation, for example, augments the beneficial effects of antipsychotics for the treatment of schizophrenia. (Tsai, G., et al., Biol. Psychiatry (1998) 44(11): 1081–1089.) L-tryptophan or 5-hydroxytryptophan supplementation has been shown to improve symptoms of depression, anxiety, insomnia and pain in patients with fibromyalgia. (Juhl, J. H., Altern. Med. Rev. (1998) 3(5): 367–375.) Dietary supplementation with 8 essential and 9 nonessential amino acids provided improved health, tone, and mood in dialysis patients, in whom protein malnutrition is a common problem. (Mastroiacovo, P., et al., Clin. Ther. (1993) 15(4): 698–704.) Nutritional supplementation with aspartic acid has been suggested for the treatment of Canavan disease, a rare recessive autosomal genetic disorder generally resulting in death within several years of onset. (Baslow, M. H., et al., J. Mol. Neurosci. (1997) 9(2): 109–125.) L-lysine has also been demonstrated to have therapeutic use for lesions associated with herpes simplex virus type 1 (HSV-1). (Ayala, E. And D. Krokorian, J. Med. Virol. (1989) 28(1): 16–20.)

Glutamine supplementation has been shown to provide numerous benefits, including stimulation of certain cells of the immune system and general promotion of cellular growth. Depletion of glutamine results in atrophy of epithelial tissue, with associated bacterial translocation. Clinical supplementation of glutamine reduces epithelial atrophy and accelerates recovery.

Dietary glutamine supplementation has been proposed for the treatment of patients recovering from surgery or suffering from sepsis, inflammation, burns, or trauma. Topical administration, usually in the form of a "swish and swallow" solution for oral use to repair the damaged epithelial tissue of mouth or esophageal sores, can be effective in many patients who have undergone bone marrow transplantation or chemotherapy. (Skubitz, et al., J. Lab. Clin. Med. (1996) 127(2): 223–8; Anderson, et al., Bone Marrow Transplant (1998) 22(4): 339–44.) Formulations for the administration of amino acids, particularly glutamine, are described in U.S. provisional patent application No. 60/134,442 filed May 17, 1999 and incorporated by reference herein.

The effectiveness of amino acid supplementation has been limited in some individuals due to aging or disease. Effective supplementation with certain amino acids is further limited to varying degrees by the low aqueous solubility and limited cellular uptake of some amino acids. Glutamine, for example, exhibits a low solubility in water (48 g/l at 30° C., 26 g/l at 18° C., 18 g/l at 0° C.; The Merck Index, 12th Edition) and a low chemical stability in aqueous solution (11 days at 22–24° C.). (Cardona, P., Nutr. Hosp. (1998) 13(1): 8–20.).

Transport of small molecules into various cell types is controlled by alternate transport systems, making it more difficult to devise methods for increasing cellular uptake into particular cell types. Despite the need for methods to enhance the uptake of amino acids and other small molecules, methods for increasing initial direct absorption of amino acids, peptides and other compounds into cells such as epithelial cells, the type of cells initially responsible for initial uptake of many bioactive compounds, has not been described.

Therefore, a continuing need exists for methods to increase cellular uptake of bioactive compounds into mammalian cells.

SUMMARY OF THE INVENTION

The invention provides a composition and a method for increasing cellular uptake of bioactive agents, particularly those compounds termed "small molecules" into the cells of mammalian tissue, such as the epithelial cells of the mucosa. The composition is a solution dispersion or suspension comprising an aqueous vehicle and an effective amount of a bioactive compound, in combination with an amount of carbohydrate effective to reduce the absolute solubility of the bioactive agent in the aqueous vehicle, so as to achieve increased transport (absorption) of the bioactive agent into the target cells. The transport (absorption) is increased over the amount that would enter the cells under physiological conditions, i.e., under homeostatic conditions, when the cells are contacted with the agent dissolved or suspended in water or in a physiological salt solution. Preferably, the transport (absorption) is increased by a factor of at least about 100–2000 times that is obtainable by a saturated aqueous solution of the active agent. It is believed that the carbohydrate(s) act by reducing the amount of free/available water in the composition, which induces increased transport into mammalian cells, in vitro or in vivo.

The carbohydrate carrier can comprise a monosaccharide, such as glucose, a disaccharide, such as sucrose, or a combination of monosaccharides and disaccharides. The carbohydrate carrier can also comprise a sugar alcohol such as mannitol, sorbitol or xylitol. The carbohydrate carrier can also comprise a polysaccharide such as high fructose corn syrup or corn syrup solids, wherein the corn syrup or corn syrup solids, hydrous or anhydrous, constitute a solution phase for the active agent(s). The carrier can be combined with water, or with a mixture of water with pharmaceutically acceptable alkanols, alkylene glycols or polyols such as glycerol, to form a solution. Preferably the organic solvents constitute a minor proportion of the aqueous phase, preferably $\leq$5–10 vol-%.

The solution can be a true solution or a flowable "solid solution." It can be administered by a variety of means for the administration of liquids, including toothpaste, chewing gum, hard or soft gelatin capsules, suppositories, or other liquid dosage forms such as topically applied lotions, drinks, such as a shake, an enema, or mouthwash.

Administration of the composition of the invention can provide treatment for a variety of physiologic disorders ameliorated by enhancement of absorption of bioactive agents into damaged or intact tissues, especially disorders affecting the endothelial cells and fibroblasts of epithelial tissue. Such physiologic disorders involving damaged tissue, include, for example, lesions of the oral and esophageal mucosa following radiation or chemotherapy in patients treated for cancer or in whom bone marrow transplant is performed, gastric and peptic ulcers, burns, major and minor trauma wounds, viral lesions, inflammatory bowel disorder, Crohn's disease, Sjoren's syndrome, xerostoma, and cryptosporidiosis.

A pharmaceutical dosage composition is also provided, consisting of either bulk-packaged or individually-packaged pre-mixed dry or liquid formulations of a therapeutically effective dose of amino acid in admixture with an amount of carbohydrate carrier effective to achieve increased absorption of the amino acid into epithelial cells. Kits can also be provided comprising, separately packaged in one container, dry formulation(s) and pre-measured aqueous vehicle(s).

DETAILED DESCRIPTION OF THE INVENTION

Figure 1:
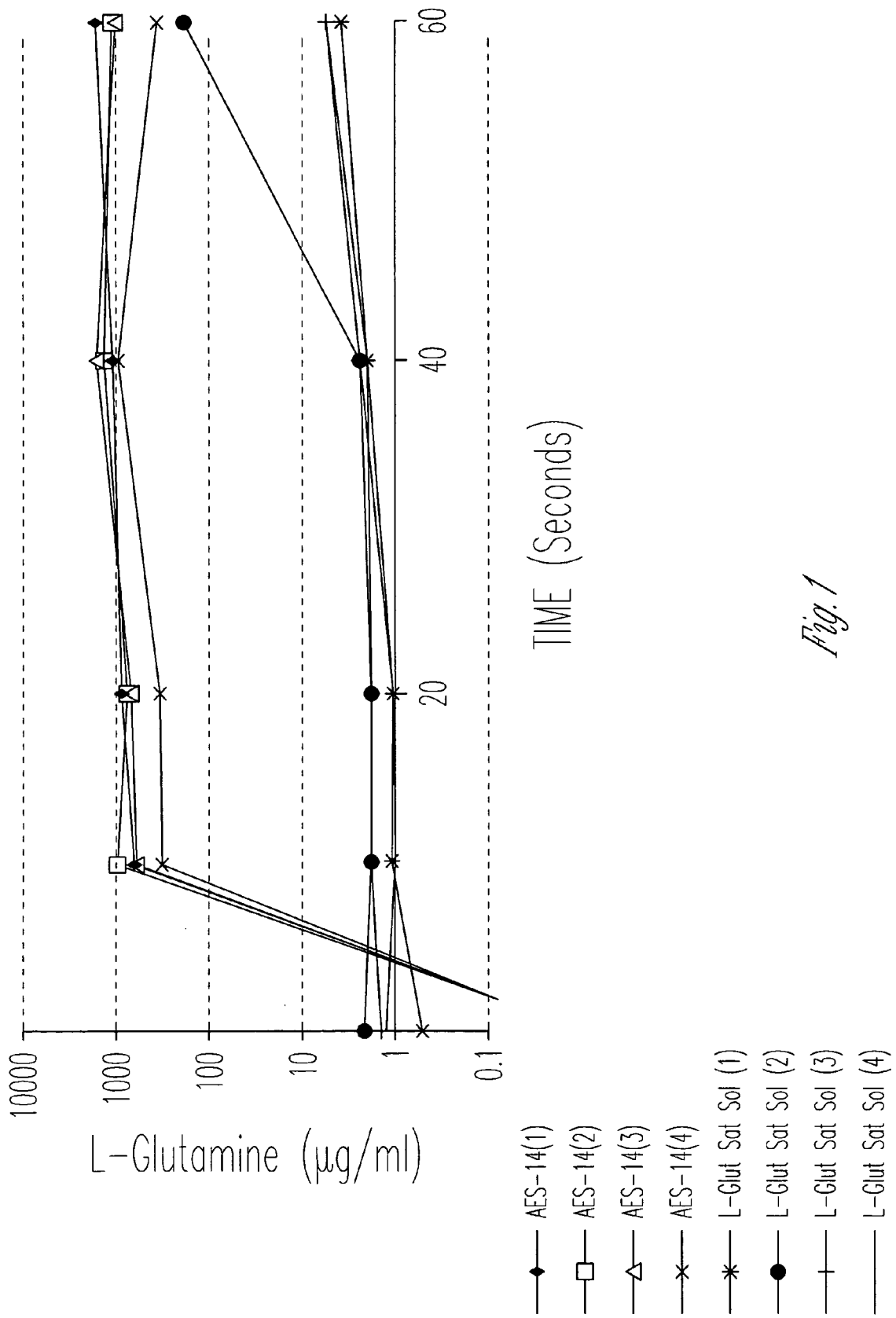
FIG. 1 and FIG. 2 are graphs illustrating the increased amino acid uptake achieved using a composition and method of the invention. The amino acid glutamine was administered to CaCo cells in combination with an effective amount of carbohydrate carrier (7:1 ratio carbohydrate carrier to amino acid)(Aesgen-14), with amino acid administered as a saturated solution without additional components (L-Glut Sat Sol) as a control. As indicated by the figure legend and the graph, intracellular glutamine concentration was increased significantly in cells treated with a combination of amino acid and carbohydrate carrier, as compared to that achieved by glutamine administration alone. Incubation time in seconds is indicated on the X axis, with cellular glutamine uptake on the Y axis.
Figure 2:
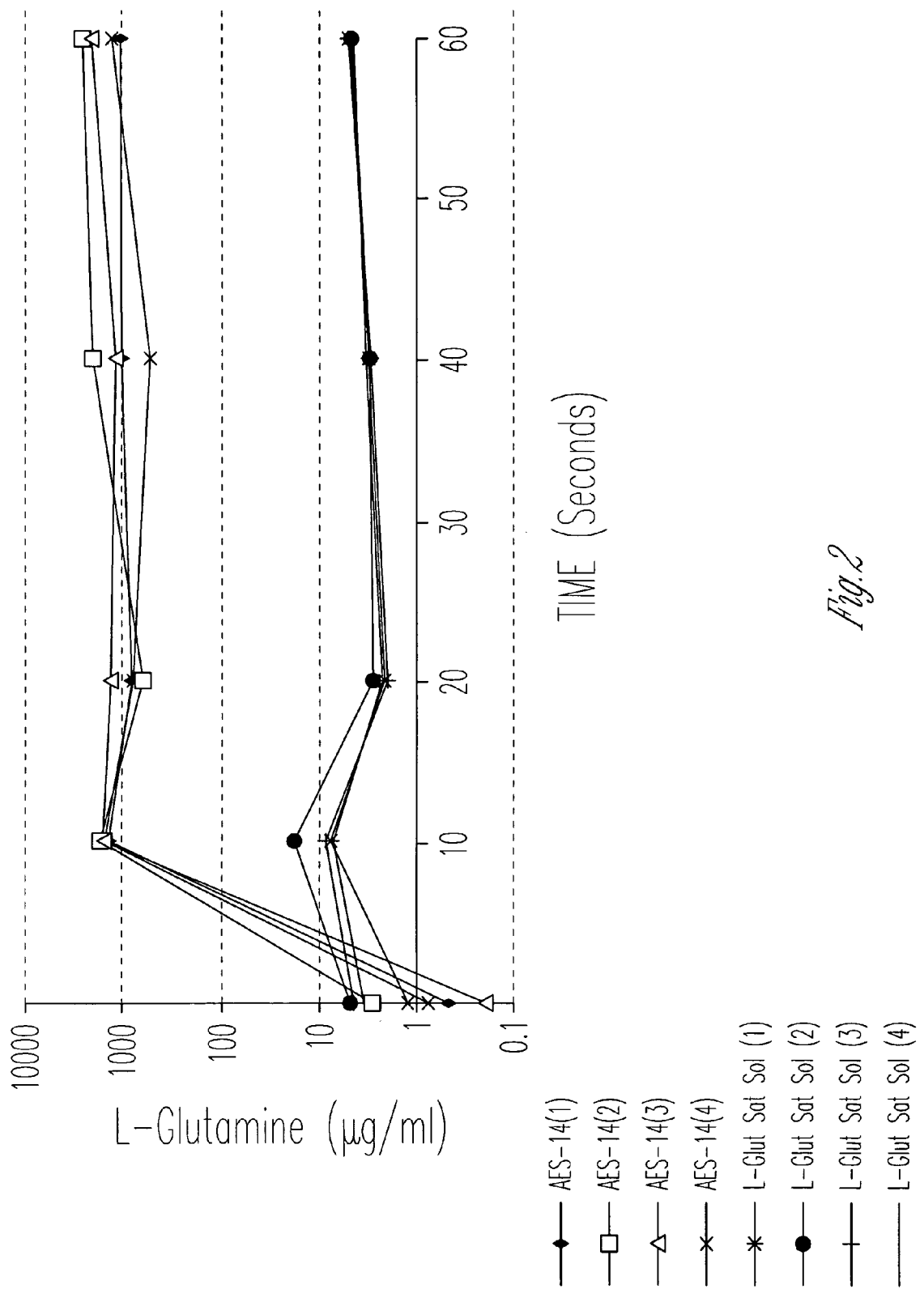
Figure 3:
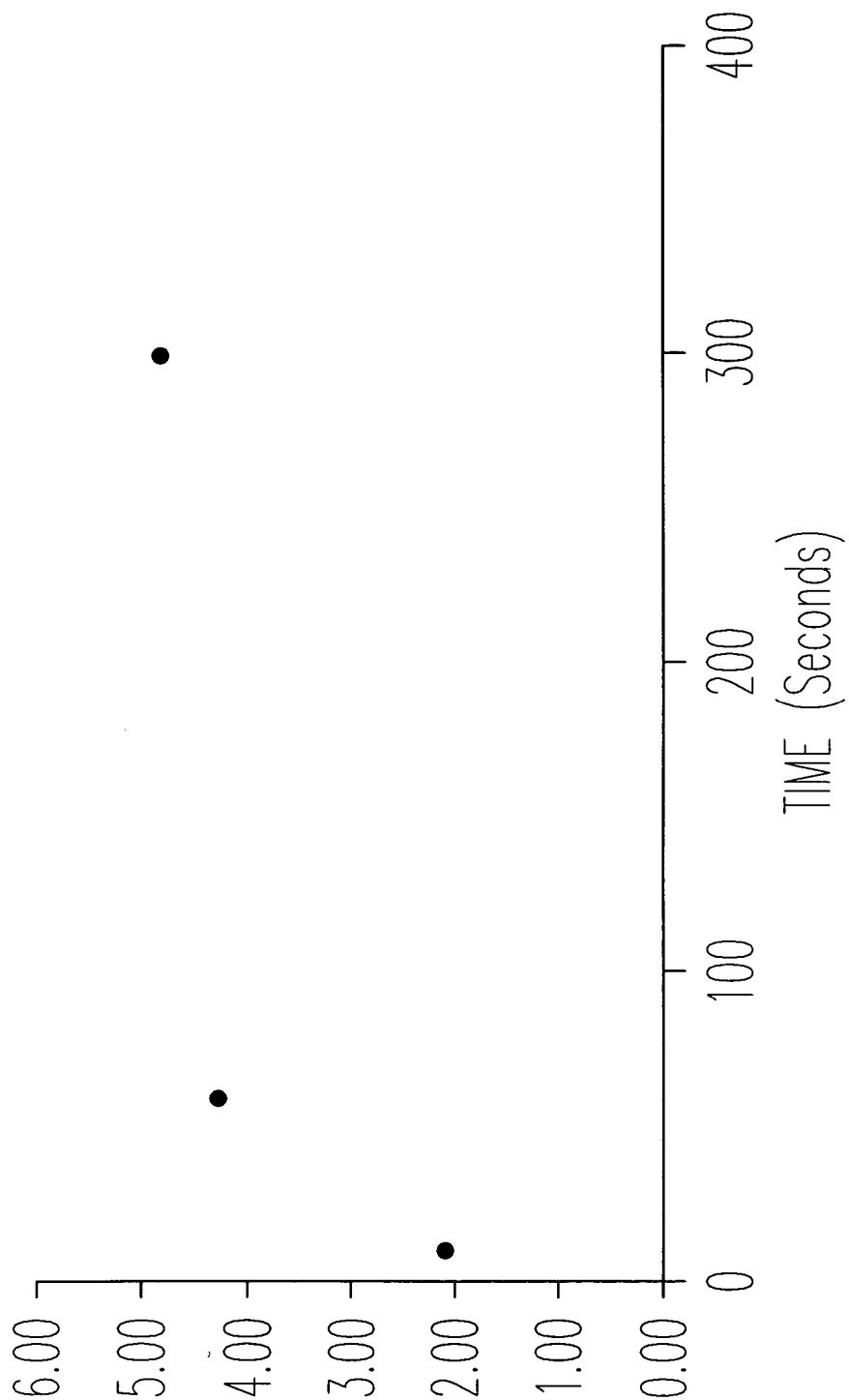
FIG. 3 depicts the relative effect of vehicle on L-glutamine cellular uptake.
Figure 4:
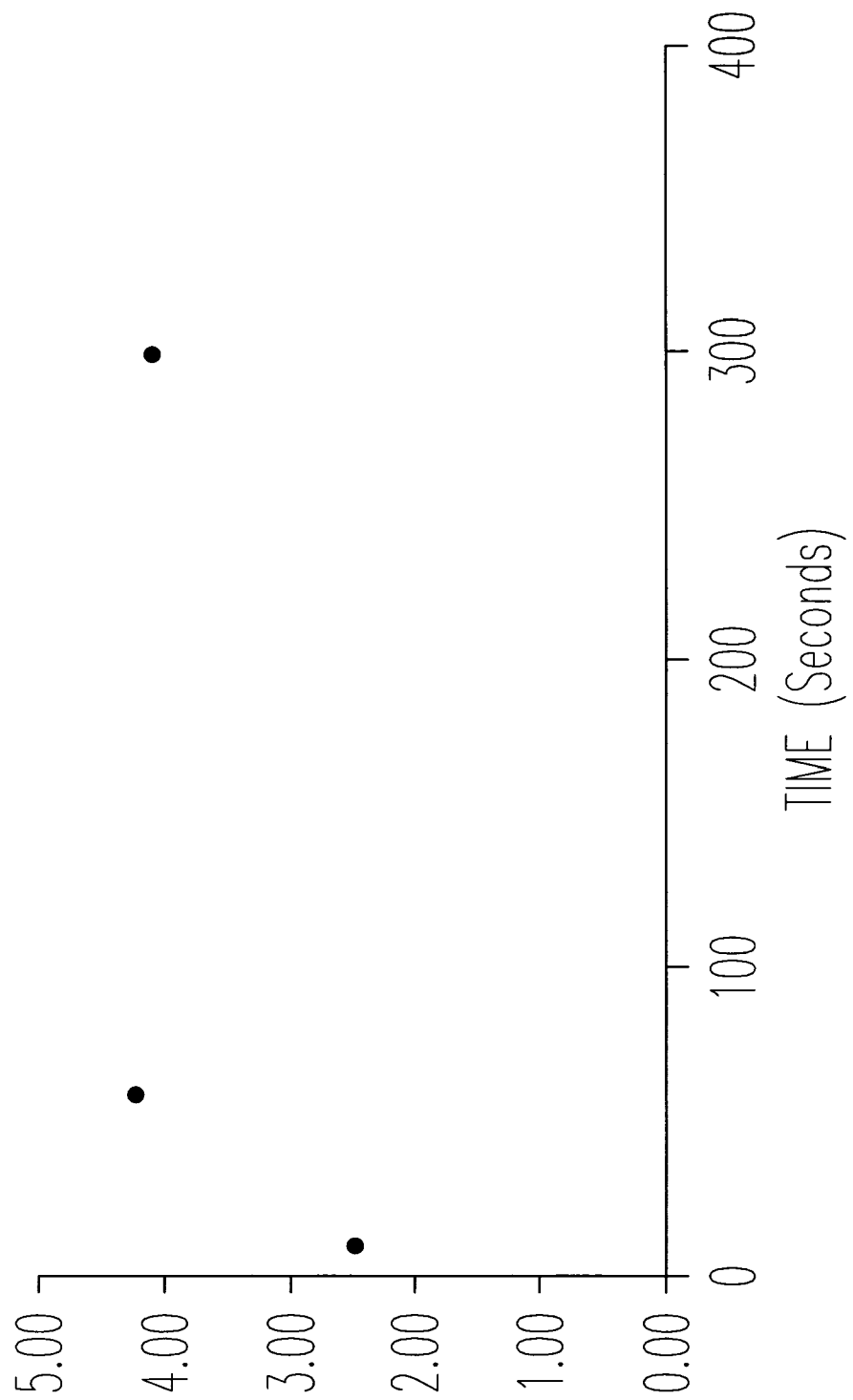
FIG. 4 depicts the relative effect of vehicle on glycylsarcosine cellular uptake.
Figure 5:
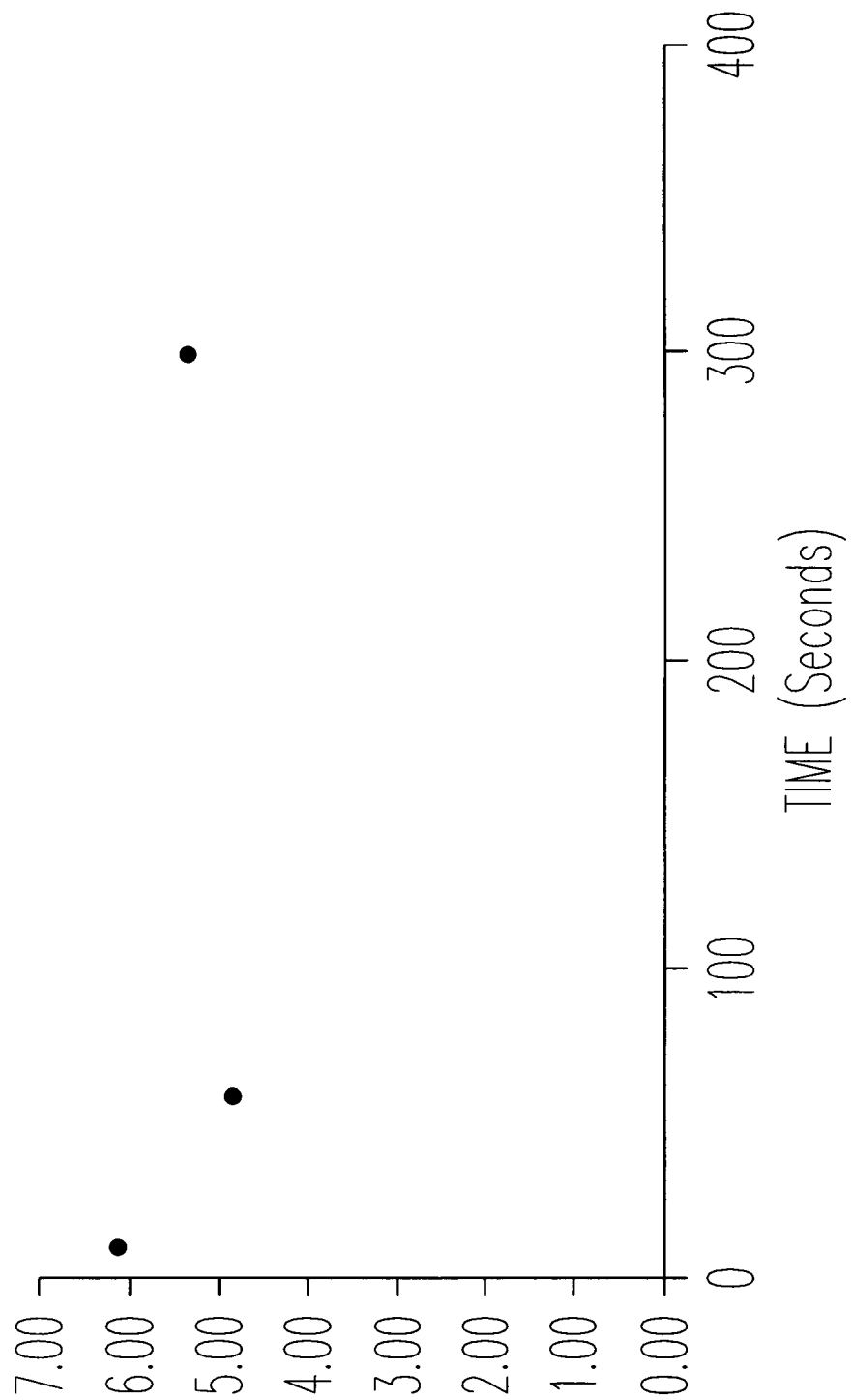
FIG. 5 depicts the relative effect of vehicle on L-asparagine cellular uptake.
Figure 6:
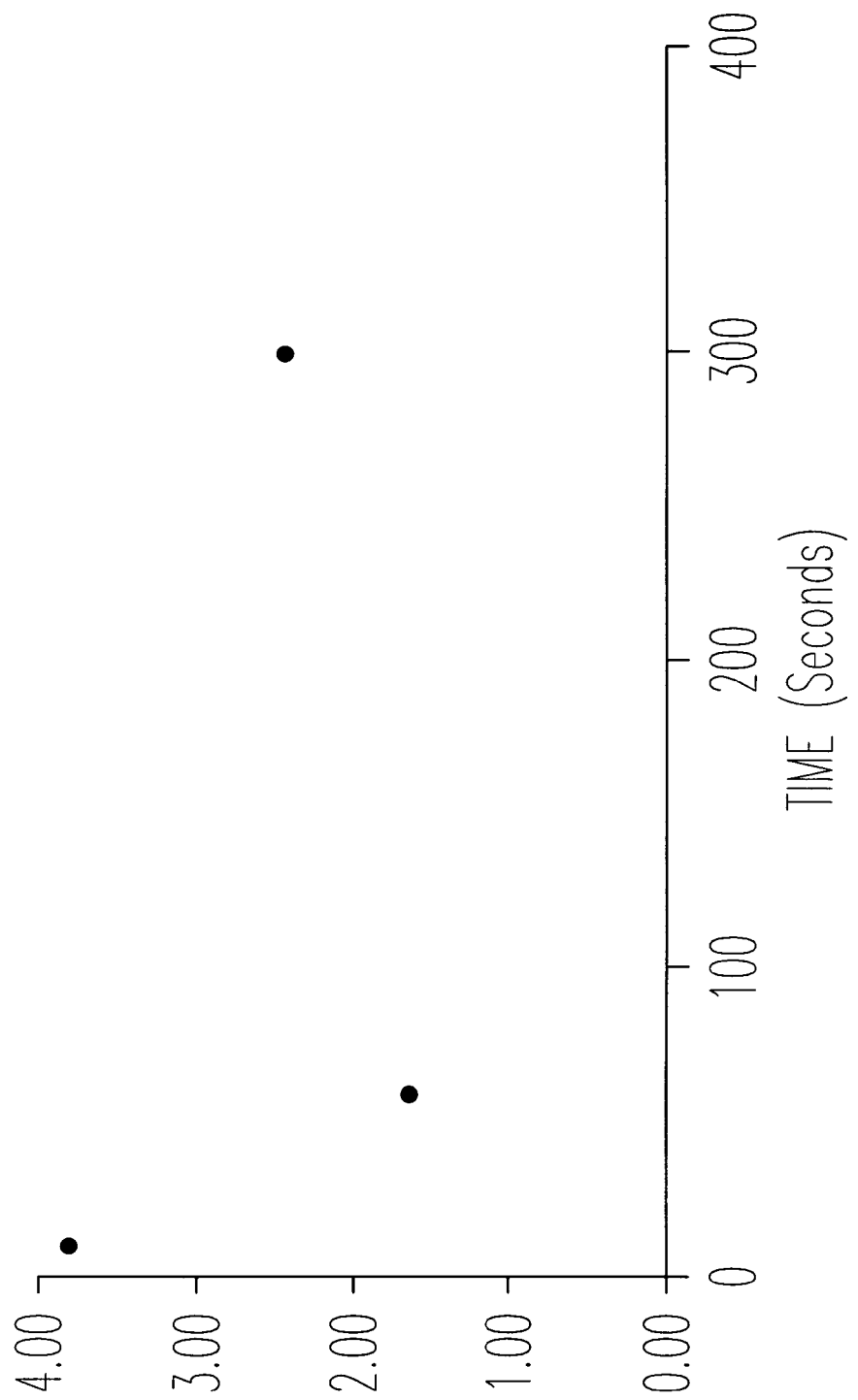
FIG. 6 depicts the relative effect of vehicle on acyclovir cellular uptake.

The inventors have discovered a new composition that increases the cellular uptake of bioactive agents into mammalian cells in vitro or in vivo. Using the composition and method of the invention, increased gastrointestinal epithelial cell uptake of the amino acid glutamine by a factor of over 150× within ten seconds after administration has been demonstrated. The present invention also provides a method for treating patients suffering from a number of pathophysiological conditions, using the composition to increase cellular uptake of bioactive agents in therapeutic amounts.

As used herein, the term "bioactive agent" refers to a molecule that exerts a therapeutic or nutritive effect on a mammal following absorption of an effective amount of the molecule by the target cells.

As used herein, the term "effective amount" refers to an amount that causes a detectable biological change in a target cell population, and preferably an amount that accomplishes a therapeutic effect, i.e., reduces at least one symptom of a pathology or disease afflicting said mammal.

As used herein, "amino acid" includes, for example, alanine, arginine, aspartic acid, asparagine, cysteine, glutamic acid, glutamine, glycine, histidine, isoleucine, leucine, lysine, methionine, phenylalanine, proline, serine, threonine, tryptophan, tyrosine, valine, citrulline, g-aminobutyric acid, hydroxyproline, and ornithine, as well as dipeptides such as glutamyl glutamate and tripeptides such as glutathione. (See *Remington's Pharmaceutical Sciences* (19th ed.) at pages 389–392.) The composition and method are particularly useful, however, for increasing absorption of those amino acids which exhibit limited aqueous solubility and/or poor cellular uptake, such as glutamine. Limited aqueous solubility, as used herein, is defined as a solubility of less than about 5 grams amino acid in 100 ml water at 22–25° C.

The present solutions can also enhance the in vitro or in vivo cellular absorption of a wide variety of bioactive agents, preferably in therapeutic amounts, particularly of the entities generally referred to as "small molecules."

As used herein, the term "small molecule" includes single molecular entities such as amino acids, steroids, cytokines, hormones, hormonal regulators, enzymes, vitamins and the like that generally have a molecular weight of less than 30 kD, preferably less than 25 kD, most preferably less than 10 kD, i.e., a molecular weight of $\leq 5000$ daltons.

As used herein, the term "oligopeptide" is a peptide comprised of 2 to 20 amino acids.

Enhanced absorption of bioactive agents into the skin or intact mucosal tissue of the gut can also be used to administer bioactive agents having an effect on organs or tissues remote from the site of administration. Such agents can include small molecules such as enzymes (enzyme deficiencies), short chain fatty acids (IBD), pamidronate (osteoporosis), pyruvate (kidney failure), interferons (immunoregulation), TGF-$\beta$ (atherosclerosis), hormones (prostate, breast and other cancers), steroids (testosterone), and chemotherapeutic agents (taxol, TMX and the like).

Other small molecules that may be potentiated using the present method include antiviral drugs and antibiotics such as those agents that ligate to binding sites or receptors on the exterior surface of the cell membrane. These antiviral agents may include analogs of the viral binding amino acid sequences or analogs of receptor groups, which inactivate the binding sequence of the virus, or toxins that are attached to receptor ligands which are used as a lethal agent to kill the infected cell, or agents that slow viral replication by inhibiting reverse transcriptase. (See *Remington's Pharmaceutical Sciences* (19th ed.) at pages 1237–1241.)

Analogs of nucleosides, nucleotides or nucreosides may be used as antiviral agents as well. Additional antiviral agents include macrophages activated by muramyl tripeptides or other ligands on liposomes; antiseptics; astringents; and B-propiolactone.

Specific antiviral agents include acyclovir, acyclovir sodium, amantadine hydrochloride, cytarabine, idoxuridine, ribavirin, rifampin, suramin, trifluridine, vidarabine, zidovudine (AZT or ZDY), HPA-23, abacavir (Ziagen®), and any of the interferons and any combination thereof. Additional antiviral agents include rCD4-ricin A chain complex; AL-721 which is a combination of tumor necrosis factor and gamma-interferon; ampligen, which is poly-IC12U; ansamycin (Rifabutin); (E)-5-(2-bromovinyl-2'-doxyuridine) (BVDU); butylated hydroxytoluene; castanospermine; dextran sulfate; dideoxycitidine (DDC); dideooxyadenosine; dideoxyinosine (DDI); foscarnet; dihydromethylpyridinyl-carbonyloxyazidodide-oxythymidine; 2'-fluoro-2'-deoxy-5-iodo-ara C (FIAC) and its uridine analog (FIAU); ganciclovir (9-[2-hydroxy-1-(hydroxymethyl) ethoxymethyl] guanine (DPHG); Peptide-T; phosphonoformate (foscarnet sodium); rimantadine hydrochloride; and any combination thereof.

Other bioactive proteins that may be potentiated using the present method include the group of proteins that are generally referred to as nerve growth factors. These include nerve growth factor itself (NGF), Brain-Derived neurotrophic factor (BDNF), neutrotrophin-3 (NT-3) and ciliary neurotropic factor (CNTF). NGF (total dose infused i.v. =1 ug) has been reported to ameliorate cholinergic neuron atrophy and spatial memory impairment in aged rats by W. Fischer et al., *Nature,* 329, 65 (1987). Recombinant human beta NGF has been produced which has potent in vitro and in vivo neurotropic activity. See J. Barrett et al., *Exp. Neurol.,* 110, 11 (1990). Therefore, exogenous administration of neuronal growth factors may be helpful to treat pathological disorders involving degenerative processes, including Alzheimer's disease or diabetic associated polyneuropathy.

The present method can also be used to deliver insulin. Since it has been demonstrated that there is a widespread distribution of insulin receptors in brain, insulin is likely to also have important functions in the central nervous system. It is suggested that insulin may function as a neurotrophic factor and neuromodulator by D. G. Baskin et al., *Trends Neurol.,* 11, 107 (1988) and D. G. Baskin et al., *Ann. Rev. Physiol.,* 49, 335 (1987).

Another class of proteins are the neuroreceptors or soluble peptides isolated therefrom. These include receptors for neurotransmitters (epinephrine, norepinephrine, dopamine, serotonin, GABA, glycine, glutamate, and the like); neuropeptides (β-endorphin, enkephalins, somatostatin, neurotensin, angiotensin vasoactive intestinal peptide, and the like); and neurohormones (luteinizing hormone releasing hormone, thyrotrophin-releasing hormone, substance P, and the like).

High molecular weight bioactive agents can also be employed in the present method and compositions, including nucleic acids such as DNA and RNA, i.e., linearized or plasmid DNA. The DNA can encode "sense" or antisense RNA to block an undesirable cellular function. The DNA can encode polypeptides such as hormones, and cytokines in amounts effective to accomplish "gene therapy," i.e., the correction of metabolic diseases and defects.

"Carbohydrate," as used herein, includes those sugars known as monosaccharides and disaccharides, polyols, hydroxy analogs or sugar alcohols, such as, for example, xylitol, sorbitol, and mannitol, and their polymers, such as dextrins, high fructose corn syrup, and corn syrup solids. It is well known in the art that certain mono- and disaccharides form sugar alcohols, or hydroxy analogs. Certain of these hydroxy analogs, particularly sorbitol and xylitol, have proven to provide the benefit of a sugar taste without the cariogenic properties of the mono- and disaccharides from which they are derived.

It is believed that the carbohydrate, or mixture thereof, as used in the present invention, acts at least in part by reducing the free water available to solubilize the bioactive agent(s), thereby promoting absorption of the amino acids into the cytosol of the target cells. Preferably, there will be a major proportion by weight of carbohydrate in the final composition, e.g., greater than 80–90 weight percent. In some cases the composition can be essentially free of added water, i.e., can be a "solid solution," the carbohydrate acting as a "solvent" for the active ingredient. Such "solid solutions" can be flowable, semisolid or even solid. The ratio of carbohydrate to active agent can be approximately 1.5:1 w/w to 20:1 w/w in a dry preparation, and preferably 4:1 w/v to 15:1 w/v in final aqueous solution, most preferably greater than 7:1 w/v, achieved either by constitution of the preparation with aqueous solvent or by delivery into the aqueous environment of the extracellular fluids surrounding the target tissue.

"Cell," as used herein, includes any cell that can be contacted by the present composition in accord with the present method, such as epithelial cells, endothelial cells, skin cells, fibroblasts or neuronal cells. More specifically, cells in which the composition and method of the present invention have been demonstrated to increase absorption of the amino acid glutamine are gastrointestinal epithelial cells., including cells of the mouth, throat, esophagus, stomach, intestines, colon and rectum, endothelial cells and fibroblasts.

"Constitution with aqueous solvent," as used herein, includes constitution with water, physiological salt solutions or buffers, fruit juice or other liquid which contains a high percentage of water, or with extracellular fluids surrounding the tissue to which the composition is applied, such as saliva, mucous, gastric fluids, spinal fluid, and the like.

Formulation of a Composition for Increasing Solubility and Absorption of an Amino Acid In accord with the present invention, at least one bioactive agent is combined with a carbohydrate in the presence of water, so as to form an aqueous solution. The carbohydrate can be a monosaccharide, including, for example, allose, altrose, arabinose, dihydroxyacetone, erythrose, erythrulose, fructose, galactose, glucose, glyceraldehyde, gulose, lyxose, idose, mannose, psicose, ribose, ribulose, sorbitol, tagatose, threose, xylose, xylulose, and their respective hydroxy analogs, such as sorbitol from sorbose, mannitol from mannose, and xylitol from xylose. Alternatively, the carbohydrate can be a disaccharide, such as maltose or sucrose, or both, or their polymers, such as dextrins, maltodextrins, and high fructose corn syrup products. The carbohydrate carrier can also be composed of any combination of monosaccharides, disaccharides, or both. For many applications, the hydroxy analog of the sugar is preferable, particularly where a noncariogenic sugar is needed. Examples of hydroxy analogs include the sugar alcohols, xylitol, sorbitol, and mannitol.

Carbohydrate concentration, measured as weight/volume, in the solid composition is preferably 20% to 99%. At a certain concentration, the carbohydrate will complex and reduce the amount of free water available as a solute for the active agent, so that the transport of the active agent into the target cell is significantly increased.

A preferred embodiment of the composition provides a mixture of solids including about 5–50% w/w glutamine (most preferably L-glutamine), about 15–50% w/w carbohydrate carriers, including a disaccharide (most preferably sucrose), a sugar alcohol or polyol (most preferably sorbitol), and glycerin, an effective amount of buffer, or buffering compound (most preferably anhydrous monobasic sodium phosphate), about 1–5% w/w modified cellulose (most preferably Avicel® Cellulose Gel), with the remainder optionally comprising stabilizers and emulsifying agents (xanthan gum, carrageenan), preservatives (methylparaben, potassium sorbate), a defoamant (simethicone), and flavoring.

A more preferred embodiment provides approximately 5–15% w/w glutamine, 30–50% w/w carbohydrate carriers, including a disaccharide (most preferably sucrose), a sugar alcohol or polyol (most preferably sorbitol), and glycerin, with the remainder of dry solids comprising an effective amount of a buffer, or buffering compound (most preferably anhydrous monobasic sodium phosphate), modified cellulose (most preferably Avicel® Cellulose Gel), and optionally comprising stabilizers and emulsifiers (xanthan gum, carrageenan), preservatives (methylparaben, potassium sorbate), defoamants (simethicone), and flavoring.

A preferred liquid composition provides 5–25% w/v L-glutamine, 20–40% w/v carbohydrate carrier, including a disaccharide, a sugar alcohol, and glycerin, 5–10% w/v citric acid, and an effective amount of buffer (preferably 0.4–0.8% sodium phosphate), with optional stabilizers, preservatives, emulsifiers and flavorings.

Use of a carbohydrate carrier in the composition can increase the cellular absorption of the amino acid by at least ten times over direct administration of the amino acid in water. For example, a preferred aqueous composition of 38% w/v L-glutamine, 30% w/v sucrose, and 2.8% w/v sorbitol produced a 360-fold increase in glutamine uptake by CaCo cells (an epithelial mucosa cell line) over that obtained by use of an aqueous glutamine solution alone.

Excipients can also be added to the composition, provided that the necessary concentration of carbohydrate carrier is maintained. These can include a sweetener/solvent, such as glycerin; emulsifying and stabilizing agents, such as cellulose gel (for example, Avicel® Microcrystalline Cellulose Gel (FMC Corp., Philadelphia, Pa.)), xanthan gum or carrageenan; preservatives and stabilizers, such as citric acid, and methylparaben; a defoamant/base ingredient, such as simethicone; flavoring, or other ingredients which improve the stability and administration of the composition.

Delivery of an Increased Concentration of an Active Agent

The invention provides a method of delivery of increased concentrations of active agent to target cells in vivo or in vitro by a number of alternate routes. For example, the active agent can be mixed with a carbohydrate and water, and optionally gelling or thickening agents. The mixture can be administered as a solution, gel, or suspension. Where desired, undissolved materials can be removed by allowing the mixture to stand to allow undissolved particles to settle out, or can be centrifuged to isolate the supernatant. The supernatant solution can then be parenterally, or orally applied to target tissue, as by intravenous injection of infusion.

Application of the preparation can include, but is not limited to, topical administration by swabbing directly on a wound resulting from, for example, burn, trauma, or viral infection, e.g., in ointment, gel or liquid form, including administration by transdermal patches. The preparation can be applied to oral, nasal, and esophageal lesions by oral rinse, a gel, or an ingestible drink. For either oral rinse or ingestible drink, the carbohydrate carrier can be chosen from among a number of monosaccharides, disaccharides, or a combination of both, or from their polymers, such as dextrins, maltodextrins, and high fructose corn syrup products. Preferred carbohydrate carriers include sucrose, sorbitol and high fructose corn syrup products. Either a suspension or a drink can be provided as a dry mixture of carbohydrate carrier and an effective amount of amino acid, for reconstitution with water, juice, or other liquid. Bulk packaging of the dry mixture or packets containing single applications can be provided to a patient, health care provider, or any individual for whom the delivery of an increased concentration of active agent is desired. Premixed liquid bulk or unit dosage forms can also be employed.

Application of the composition having a relatively low concentration of free water can also be accomplished by providing a lozenge or a form of candy or other medicated confection, such as a common lollipop, which utilizes a suitable carbohydrate carrier, such as sucrose or sorbitol, and a gelling or thickening agent, as needed. Chewing gum can also be used to deliver the carbohydrate carrier, such as sucrose, xylitol, sorbitol, or corn syrup solids, and amino acid. In a preferred form, the chewing gum can incorporate a central pocket of flavored syrup, composed of the appropriate mixture of carbohydrate carrier, such as xylose, sorbitol, or sucrose, and an effective amount of the amino acid. Formulations for preparation of chewing gum with a soft core portion are described in U.S. Pat. No. 4,352,823 (Cherukuri, et al., Oct. 5, 1982) and U.S. Pat. No. 4,352,825 (Cherukuri, et al., Oct. 5, 1982). Alternatively, a solid solution of a biologically active agent can be used in the preparation of chewing gum, lozenges, or a candy form such as a lollipop. Such solid solutions can be formed from comelts, coprecipitates, or by mechanical activation of the carbohydrate carrier and the biologically active agent.

A toothpaste can also be formed to incorporate a carbohydrate carrier and active agent. Microencapsulation of ingredients in toothpaste compositions has been described in U.S. Pat. No. 4,348,378 (Kosti, Sep. 7, 1982), U.S. Pat. No. 4,071,614 (Grimm, Jan. 31, 1978), and U.S. Pat. No. 3,957,964 (Grimm, May 18, 1976), which describe the addition of encapsulated flavorings and anti-plaque ingredients to standard toothpaste preparations.

The composition of the present invention can also be delivered by suppository to epithelial tissues of the colon and rectum. Methods of preparation of suppository formulations are known in the art. One such method has been described in U.S. Pat. No. 4,439,194 (Harwood, et al., Mar. 27, 1984), which describes a water and drug delivery system for suppository use. An enema preparation can also be formed of a carbohydrate carrier and an amino acid, incorporating a sufficient amount of water to form an aqueous solution. A solid solution of the biologically active agent in the carbohydrate carrier can also be administered in a suppository or enema, drawing the aqueous component from the colon or rectum.

When delivery to the stomach is preferred, a filled capsule can be used. One such method has been described in U.S. Pat. No. 5,569,466 (Tanner, et al., Oct. 29, 1996), which describes the preparation of fill compositions for soft elastic gelatin capsules. Enteric coated capsules or tablets, or enteric coated microparticles can be employed to deliver the compositions to the upper or lower intestines.

The composition can be delivered in ice cream formulations, as well as frozen confections such as the common popsicle. Frozen formulations can be especially effective for the treatment of oral and esophageal ulcers, since they can combine, for example, both the beneficial effects of glutamine, as well as the soothing effects of the cold mixture.

The composition of the present invention has been shown to improve solubility and cellular absorption of a dietary amino acid, glutamine, into human gastrointestinal epithelial cells, as illustrated in the following example.

EXAMPLE 1

Evaluation of Cellular Uptake of Glutamine in Combination With Sucrose and Sorbitol 1. Materials and Methods Distilled, deionized water (107 ml) was added to 207 grams of a mixture of sucrose, sorbitol, and glutamine with excipients (Aesgen-14) as listed in Table 1.

TABLE 1

| Aesgen-14 (AES-14) | | | |
|---|---|---|---|
| L-glutamine | 240.0 Kg | 57.94 w %* | 50.00% w/v** |
| Sucrose | 144.0 Kg | 34.77 w % | 30.00% w/v |
| Crystalline Sorbitol | 13.44 Kg | 3.24 w % | 2.80% w/v |
| Glycerin | 14.0 Kg | 2.92 w % | 2.52% w/v |
| Sodium Phosphate Monobasic (Anhydrous) | 2.6 Kg | 0.63 w % | 0.54% w/v |
| Avicel Cellulose Gel Type CL-611 | 874.0 g | 0.18 w % | 0.17% w/v |
| Citric Acid (Anhydrous) | 280.0 g | 0.07 w % | 0.06% w/v |
| Xanthan Gum | 230.0 g | 0.05 w % | 0.04% w/v |
| Carrageenan | 230.0 g | 0.05 w % | 0.04% w/v |
| Artificial Flavor | 230.0 g | 0.05 w % | 0.04% w/v |
| Methylparaben | 207.0 g | 0.04 w % | 0.04% w/v |
| Potassium Sorbate Powder | 180.0 g | 0.04 w % | 0.04% w/v |
| 30% Simethicone Emulsion | 115.0 g | 0.02 w % | 0.02% w/v |

*Weight percents are expressed as percent of total weight of dry ingredients for reconstitution with water in a 240 ml bottle.
**Weight/volume percents are expressed as percent of total volume in aqueous mixture.

As a control, 200 milliliters of distilled, deionized water was added to 50 grams of L-glutamine (Ajinomoto, Raleigh N.C.) and mixed by agitation. Both samples were allowed to stand for 1 day at room temperature. The supernatant was decanted from the residue and used for the cellular uptake determination.

On Day 1, cells from a human gastrointestinal epithelial cell line (CaCo) were plated at a density of $0.5 \times 10^6$ cells per well in a 6-well tissue culture dish. On Day 2, culture media was replaced with either normal growth medium or medium deficient in L-glutamine.

On Day 3, cells cultured in both normal growth medium ("normal") and L-glutamine deficient growth medium ("starved") were evaluated for comparison of glutamine uptake using the Aesgen-14 solution in parallel with the L-glutamine solution, according to the following protocol: Two milliliters of test material (either Aesgen-14 or L-glutamine solution) was added to the appropriate wells, then incubated at 37° C. At time points 0, 10, 20, 40, and 60 seconds the test material was aspirated and the cells washed three times (3×) with chilled (4° C.) phosphate buffered saline (PBS), followed by the addition of 1.0 ml of perchloric acid. Cells were harvested by scraping, then aspiration by pipet into a 1.7 ml tube.

The harvested cells were sonicated for 10 seconds, and 500 µl of sonicated cells were transferred into a 1.7 ml tube. The perchloric acid was neutralized by the addition of 130 µl of 2M KHCO$_3$, and the resulting mixture was frozen overnight at −80° C.

Upon thawing, the sample was centrifuged for 10 minutes at 14,000 rpm and the supernatants were transferred to new 1.7 ml tubes and frozen at −80° C. The resulting clarified samples were thawed and diluted 1:3 with deionized water. Fifty microliters were withdrawn, added to 10 microliters complete o-phthaldialdehyde (Sigma P-0532), and mixed by agitation. After incubation for two minutes at room temperature, a 20 µl sample was injected on a Hypersil® C18 Elite 5 µm HPLC column using 70:30 acetonitrile:water as the mobile phase. Glutamine levels, measured as µg/ml, were detected at 340 nm.

2. Results

Results are shown in Table 2 as µg/ml mean cellular glutamine uptake:

TABLE 2

| | Incubation Time (Seconds) | | | | |
|---|---|---|---|---|---|
| | 0 | 10 | 20 | 40 | 60 |
| Normal cells + Aesgen 14 | 1.00 | 1568.55 | 900.60 | 1185.88 | 1765.13 |
| Normal cells + L-glutamine | 3.53 | 10.30 | 2.48 | 3.23 | 4.85 |
| Starved cells + Aesgen 14 | 0.00 | 613.10 | 672.93 | 1213.40 | 1053.85 |
| Starved cells + L-glutamine | 1.33 | 1.43 | 1.49 | 2.23 | 49.96 |

As summarized above, glutamine uptake is significantly increased in both normal cells (363×) and in starved cells (21×) in cells treated with Aesgen-14 as compared to cells treated with aqueous L-glutamine alone.

EXAMPLE 2

Effect of AES-14 on Drug Uptake and Permeability

The cellular uptake and permeability enhancing effect of a pharmaceutical vehicle on four model drugs (L-glutamine, L-asparagine, glycylsarcosine, acyclovir, along with half saturation L-glutamine) across Caco-2 cell monolayers were measured in this experiment. Uptake and permeability of each compound was measured in the apical-to-basolateral direction, with and without vehicle.

Methods

Materials. Two amino acids (L-glutamine, L-asparagine), a dipeptide (glycylsarcosine), and a therapeutic agent (and acyclovir) with low permeability were studied. Each compound was tritiated. $^{14}$C-mannitol was used as an evaluation of monolayer/cell integrity (i.e. as a low uptake/permeability marker).

Uptake and Permeability Assessments. Compound cellular uptake into and permeability across Caco-2 monolayers was measured. Caco-2 monolayers were grown using a recently developed, rapid culture system, that requires 4 days rather than 21 days. Lentz et al., (2000), *Int. J. Pharm.*, 200(1): 41–51.

Uptake and permeability studies were conducted in duplicate at 37° C. and 50 oscillations per min across Caco-2 monolayers in either (a) blank AES-14 (i.e., AES-14 without L-glutamine) or (b) Hank's balanced salt solution (HBSS) containing 10 mM HEPES buffer (solution pH=6.8). HBSS was used when no pharmaceutical vehicle was present for each of the four compounds. Blank AES-114 was the matrix for L-asparagine, glycylsarcosine, acyclovir, and "half-saturation" L-glutamine studies when a vehicle effect is considered. AES-14, which contains L-glutamine, was studied for L-glutamine. Monolayer integrity was monitored using $^{14}$C-mannitol permeability. Mannitol uptake was also studied.

Uptake and permeability studies were conducted using Transwell® inserts in the apical to basolateral direction, at intervals of 10 sec., 60 sec., and 5 min. Donor solution included a nine saturated systems (except half strength L-glutamine) were the source solutions for the uptake/permeability studies. Saturated solutions were obtained by utilizing 5.4 g L-glutamine/100 ml, 1 g L-asparagine/10 ml, 2 g glycylsarcosine/10 ml, and 16 mg acyclovir/10 ml system concentrations (Kristol, (1999), *J. Pharm. Sci.*, 88: 109–110), wherein excess solid solute was present to assure saturation:

Saturated solution of L-glutamine in HBSS (5.4 g/100 ml)

Saturated solution of L-asparagine in HBSS (1 g/10 ml)

Saturated solution of glycylsarcosine in HBSS (2 g/10 ml)

Saturated solution of acyclovir (16 mg/10 ml) in HBSS AES-14

Saturated solution of L-asparagine in blank AES-14(1 g/10 ml)

Saturated solution of glycylsarcosine in blank AES-14 (16 mg/10 ml)

2.3 g/100 ml L-glutamine in blank AES-14 (i.e. half-saturated L-glutamine)

$^{14}$C-mannitol and $^{3}$H-drugs were quantified by liquid scintillation counting. For uptake studies, at designated time points (10 sec, 60 sec, and 5 min), the donor solution was aspirated off. The cell monolayer was washed twice with ice cold HBSS to remove any residual binding and then dissolved in 1 ml of the cell solubilizing agent, Solvable®. The cell lysate (0.5 ml) was added to 5 ml scintillation cocktail (Econosafe®) and counted on liquid scintillation counter (Beckman LS5801, Columbia, Md.). For permeability studies, 0.5 ml of received solution was added to 5 ml scintillation cocktail (Econosafe®) and counted on liquid scintillation counter.

Since saturated solutions of unknown concentration of drugs were used, absolute uptake could not be calculated. Hence, the vehicle effect on uptake is considered below (FIGS. 3–7) in terms of the relative drug uptake into cell monolayer from vehicle vs non-vehicle (i.e., ratio of uptake, after normalized for slight differences in radiolabel tracer).

Permeability (3) in each experiment was calculated (FIGS. 8–12) using eq 1:

$$P = \frac{\frac{dM}{dt}}{A \cdot C_d}$$

where P is permeability, dM/dt is rate of drug mass accumulation (i.e., radioactivity) in receiver compartment, A is area, and $C_d$ is donor drug concentration (i.e., radioactivity). Polli et al., (1998), *Pharm. Res.*, 15: 47–52. Permeability is an absolute measure (units of cm/Sec or velocity) and can be determined even though the absolute drug concentrations were not known.

Results

Figure 7:
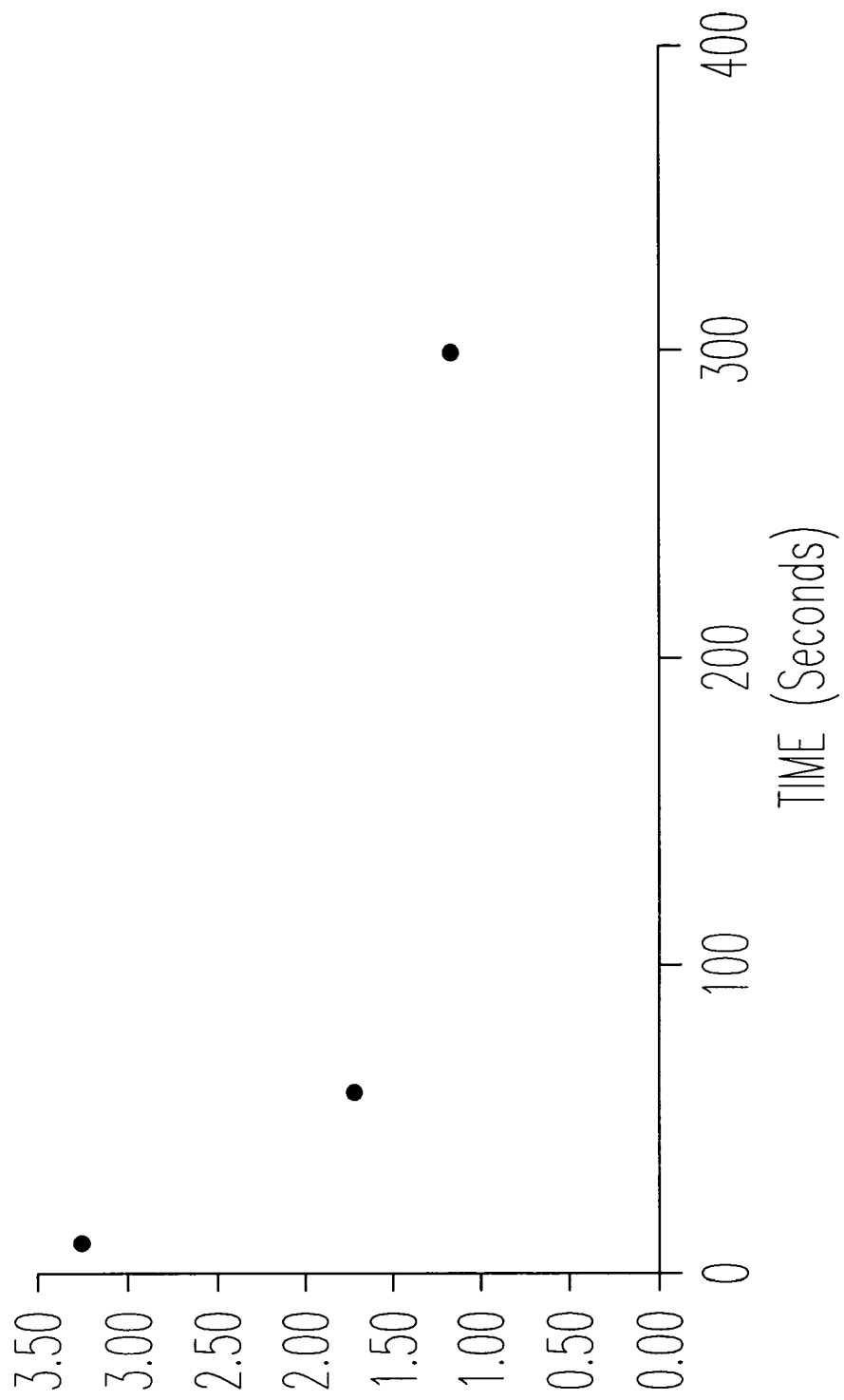
FIG. 7 depicts the relative effect of vehicle on L-glutamine cellular uptake (from half saturation).
Figure 8:
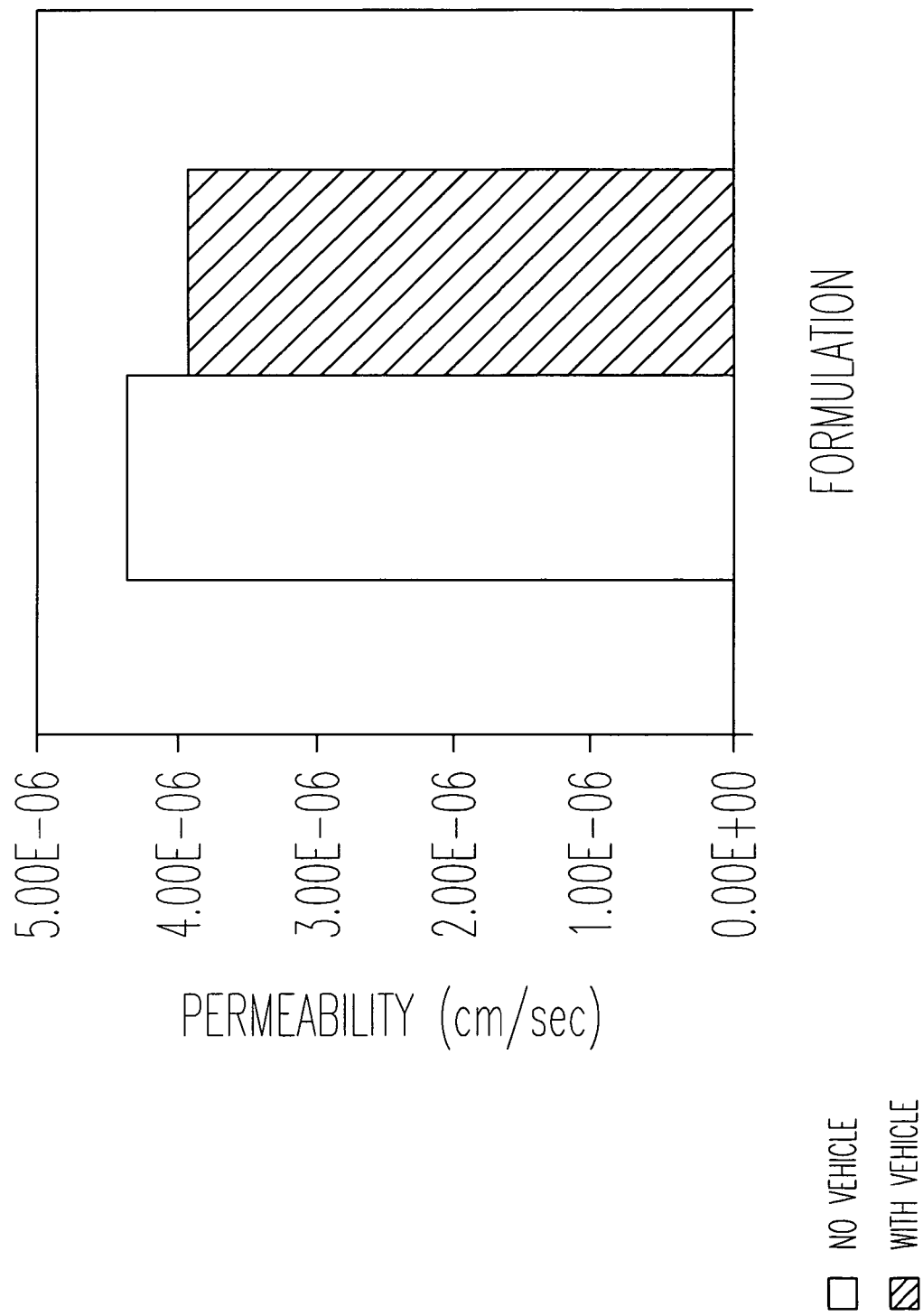
FIG. 8 depicts the CaCo-2 permeability of L-glutamine.
Figure 9:
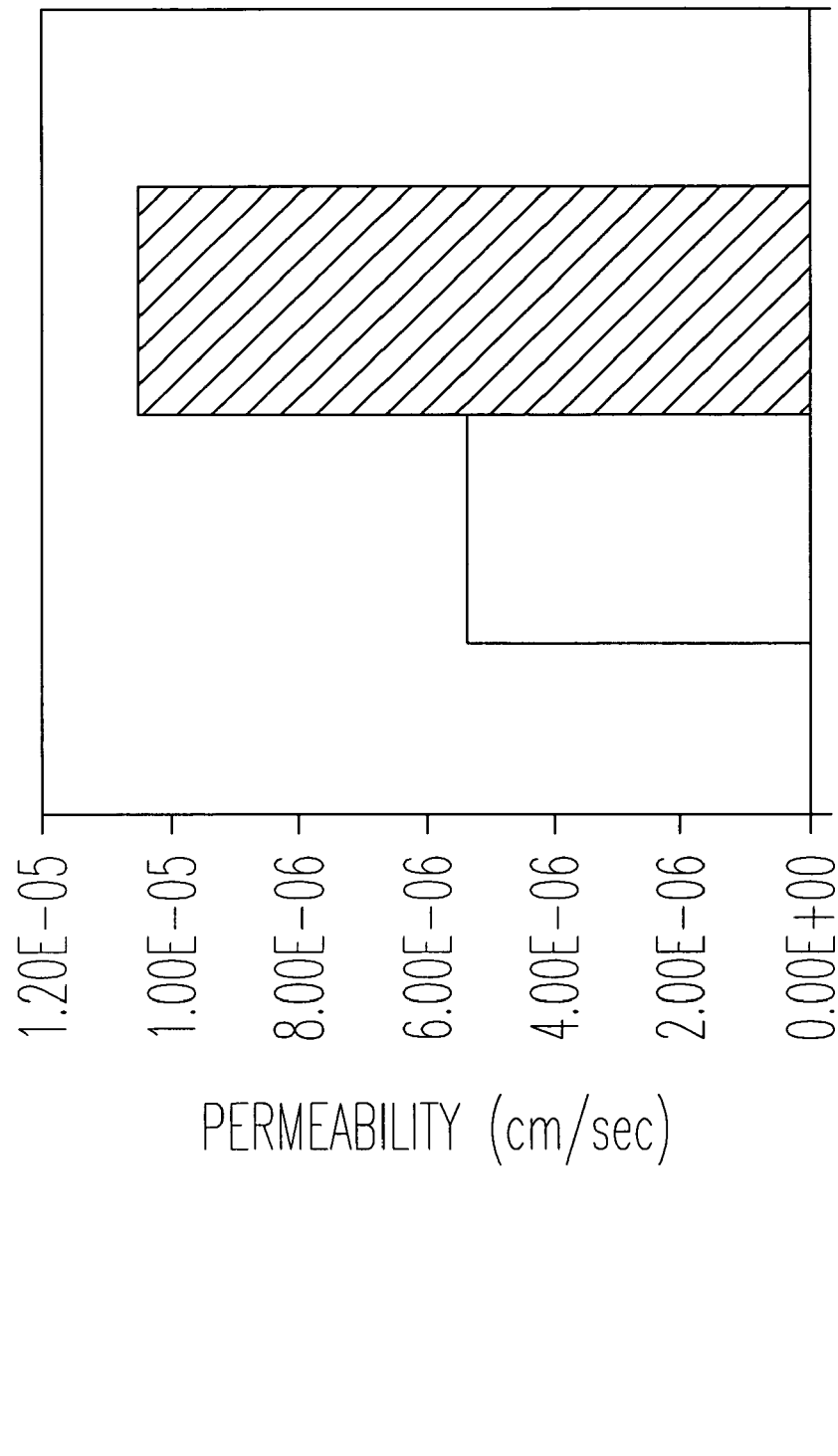
FIG. 9 depicts the CaCo-2 permeability of glycylsarcosine.
Figure 10:
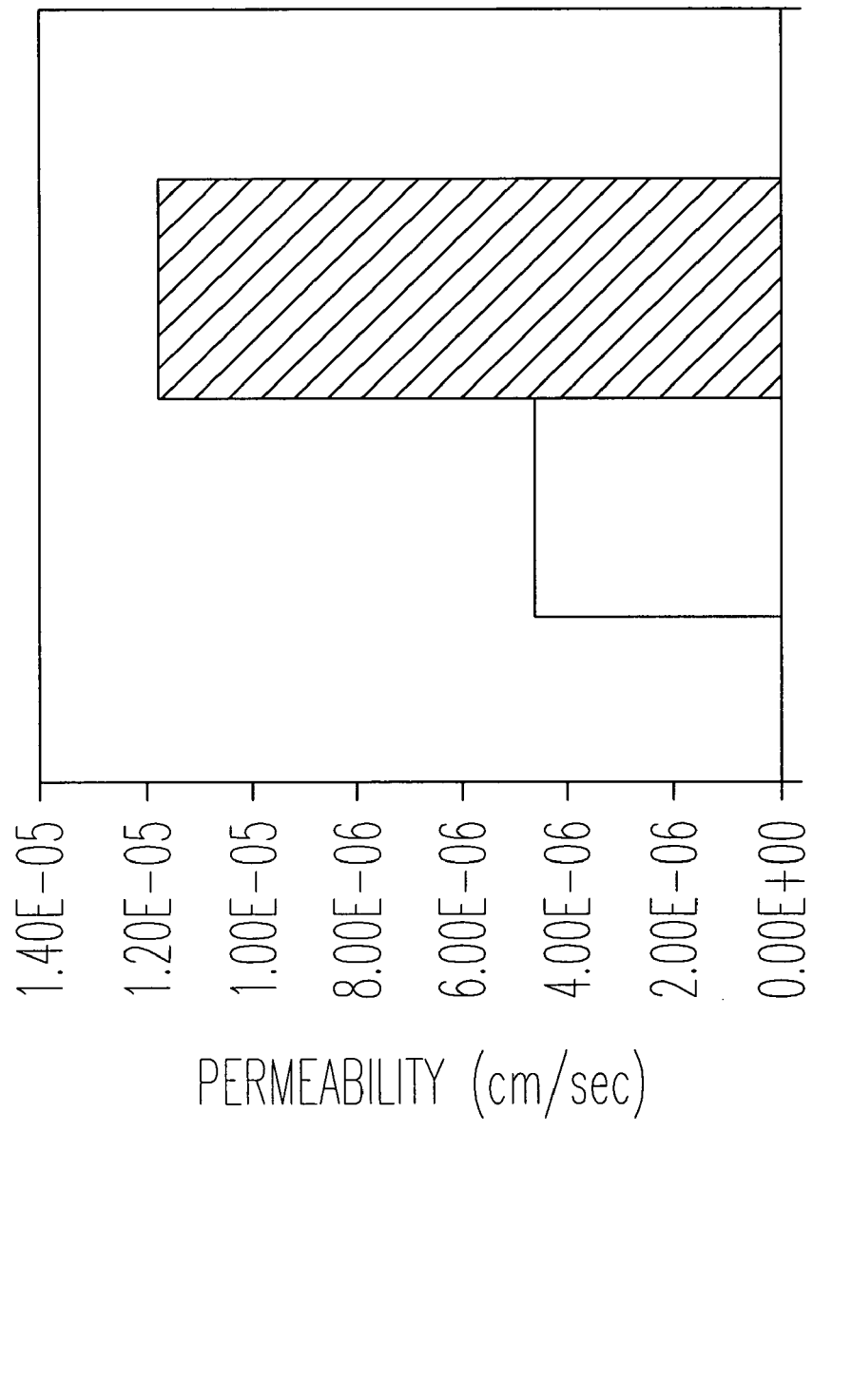
FIG. 10 depicts the CaCo-2 permeability of L-asparagine.
Figure 11:
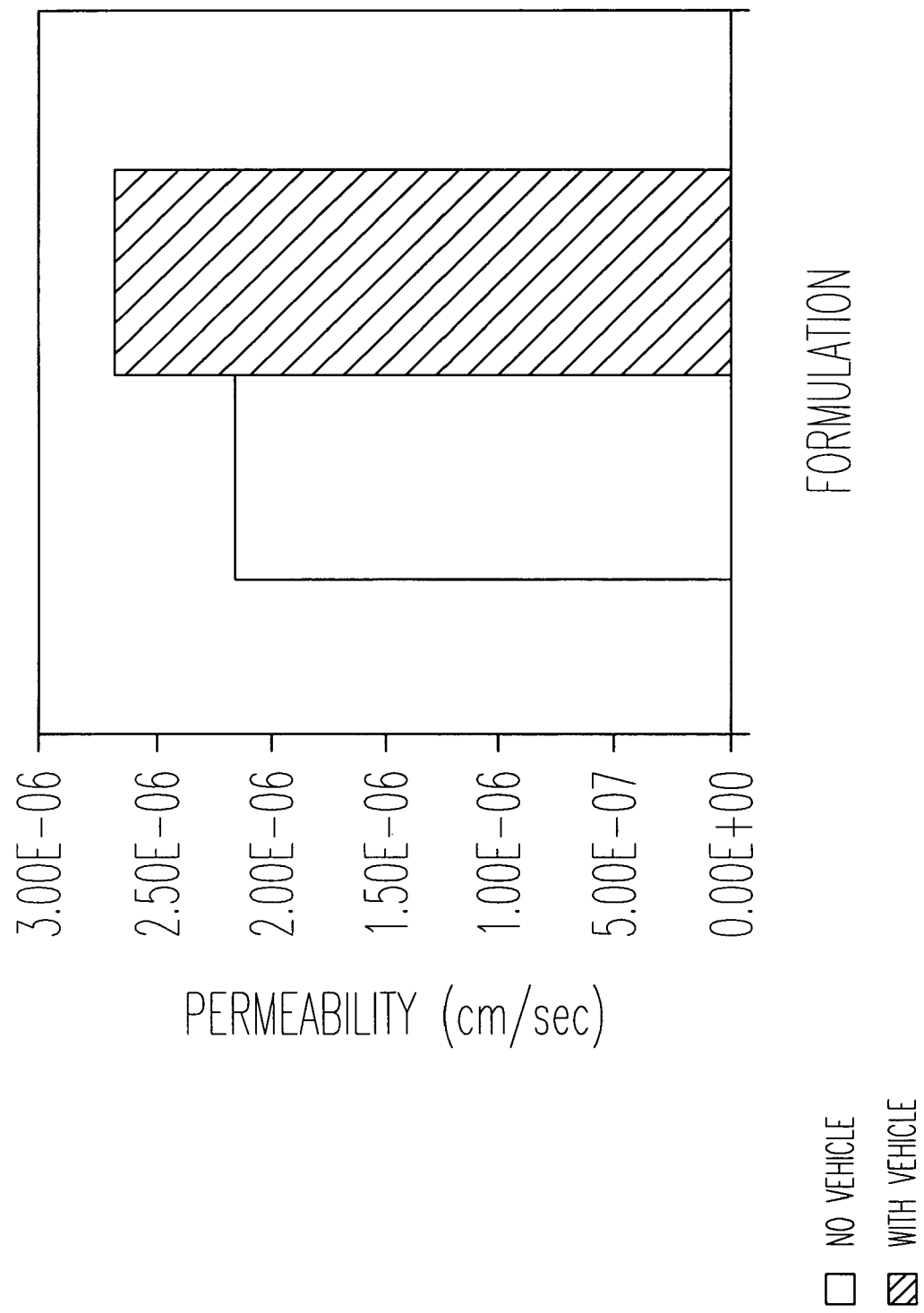
FIG. 11 depicts the CaCo-2 permeability of acyclovir.
Figure 12:
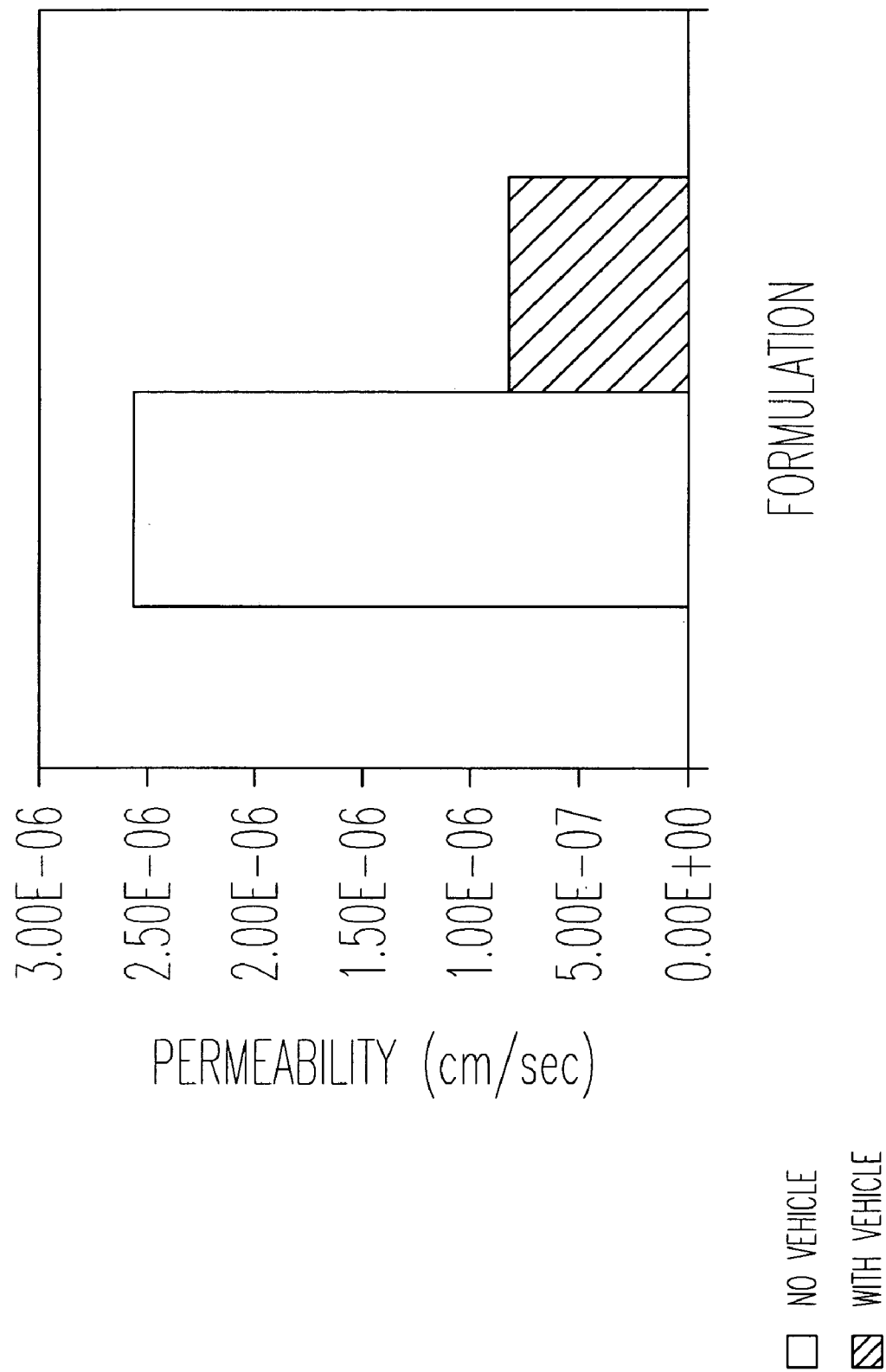
FIG. 12 depicts the CaCo-2 permeability of L-glutamine (from half saturation).
Figure 13:
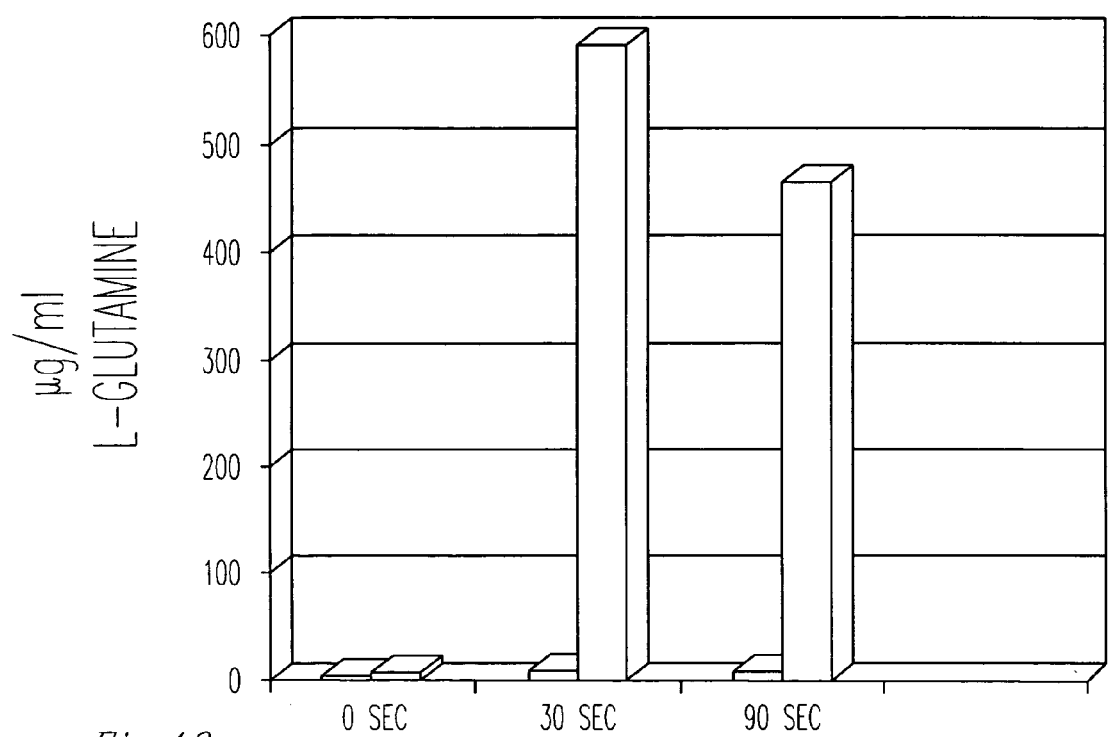
FIG. 13 depicts the effect of Aesgen-14 on L-glutamine uptake into human fibroblasts (right boxes) vs. saturated L-glutamine (left boxes).

Uptake. In FIGS. 3–7, the relative effect of vehicle on L-glutamine, glycylsarcosine, L-asparagine, acyclovir, and L-glutamine (half-strength) uptake into cells is shown. If uptake (normalized for slight differences in donor radiolabel) were identical from each vehicle and HBSS, the relative uptake would be 1.0. For all four drugs and half-strength L-glutamine, the relative uptake exceeded 1.0. In FIGS. 3–6, for L-glutamine, L-asparagine, glycylsarcosine, and acyclovir, vehicle enhanced cellular drug uptake about four-fold. To perhaps a lesser extent, vehicle enhanced half-strength L-glutamine (FIG. 7).

In Table 2 below, vehicle had no effect on mannitol relative uptake. These mannitol studies, which were performed simultaneously with those in FIGS. 3–7, indicated the vehicle effect differentiates mannitol from the other compounds, in terms of uptake enhancement. Thus, the uptake of the saccharides per se is apparently not increased, and the term "biologically active agent" can be read to exclude the saccharides present in the solution, dispersion, or gel.

TABLE 2

Relative Effect of Vehicle on Mannitol Cellular Uptake

| Time (sec) | L-glutamine study | Glycylsarcosine study | L-argine study | Acyclovir study | L-glutamine (half-strength) study |
|---|---|---|---|---|---|
| 5 | 0.52 | 0.83 | 1.65 | 1.24 | 1.20 |
| 60 | 0.80 | 1.51 | 0.77 | 0.85 | 0.57 |
| 300 | 0.63 | 1.06 | 0.43 | 0.43 | 0.30 |

Permeability. In FIG. 8–12, the relative effect of Aesgen-14 vehicle on L-glutamine, glycylsarcosine, L-asparagine, acyclovir, and L-glutamine (half-strength) permeability is shown. Unlike the uptake data presented above, which shows the relative vehicle effect on uptake (i.e., the ratio of uptake with vehicle vs without vehicle), permeability is an absolute measurement, and is calculated for each formulation (no vehicle and with vehicle). Since two-fold variation in permeability is within typical experimental variation, these results indicate that vehicle had no effect on permeability. Similarly, vehicle had no effect on mannitol permeability (Table 3).

Figure 14:
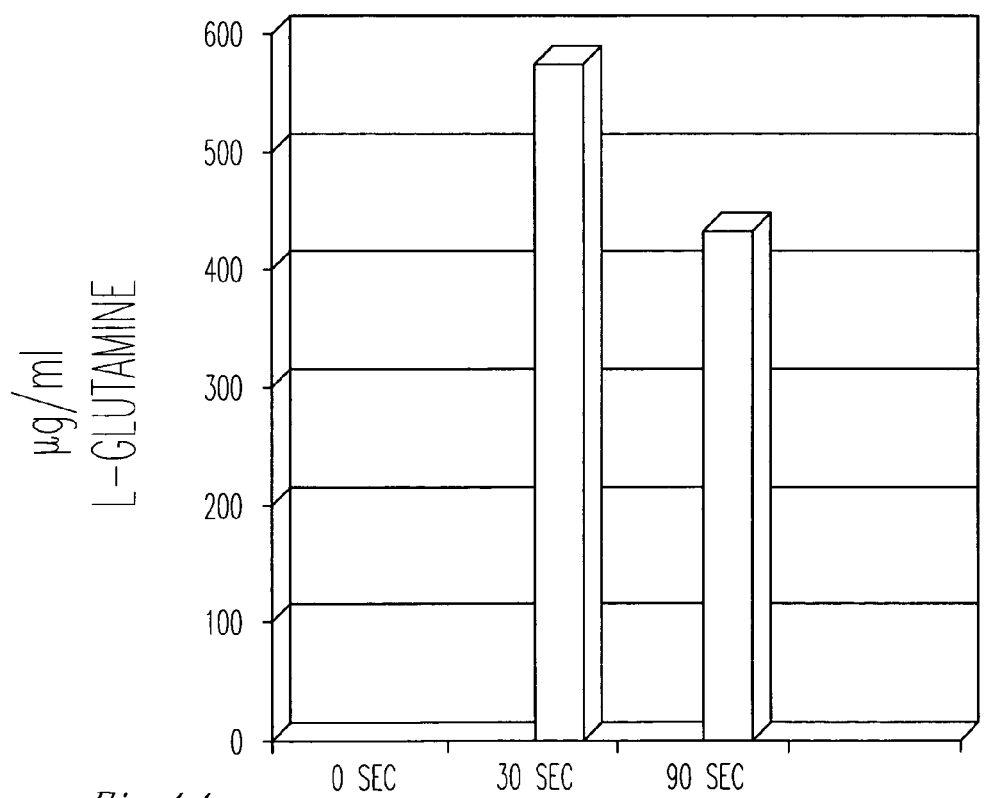
FIG. 14 depicts the effect of Aesgen-14 on L-glutamine uptake into human umbilical and endothelial cells.

In FIG. 14 the effect of Aesgen-14 vehicle on L-glutamine uptake into human fibroblasts (right boxes) vs. uptake of saturated L-glutamine (left boxes). FIG. 14 depicts the effect of vehicle on L-glutamine absorption into human endothelial cells. On the chart, the effect of saturated L-glutamine alone was not visible.

It should be noted that 5 min. represents a very brief time frame for traditional Caco-2 permeability studies. It is unlikely that steady-state is achieved after 5 min., reducing the probability of observing any possible vehicle effect.

Summary

L-glutamine, L-asparagine, glycylsarcosine, and acyclovir represent two amino acids, a peptide, and an anti-viral agent, each with poor passive membrane penetration properties under normal physiological conditions. Hence, enhancement of their cellular uptake and membrane permeability is advantageous, from a drug delivery perspective. For saturated solutions of L-glutamine, L-asparagine, glycylsarcosine, and acyclovir, vehicle AES-14 enhanced their cellular drug uptake about four-fold. This enhancement of drug uptake into cells occurred immediately (i.e., <<1 min), and was sustained over the time period studies (5 min.). To perhaps a lesser extent, vehicle enhanced half-saturated L-glutamine. Vehicle had no effect to mannitol uptake. Regarding permeability over a very brief 5 min. period, vehicle had no effect for any compound.

TABLE 3

Caco-2 Permeability of Mannitol

| Study | Mannitol Permeability without Vehicle (cm/sec) | Mannitol Permeability with Vehicle (cm/sec.) |
|---|---|---|
| L-glutamine | $3.80 \times 10^{-9}$ | $9.16 \times 10^{-7}$ |
| Glycylsarcosine | Below LOQ | $1.48 \times 10^{-6}$ |
| L-asparigine | $3.80 \times 10^{-6}$ | $9.48 \times 10^{-7}$ |
| Acyclovir | $1.14 \times 10^{-6}$ | $1.46 \times 10^{-6}$ |
| L-glutamine (half-strength) | $1.49 \times 10^{-6}$ | Below LOQ |

Method for Treating Mammalian Subjects by Enhancing Amino Acid Absorption

The composition of the present invention, and its various methods of delivery, can be used in a method for treating a variety of mammalian, especially human, physiologic disorders. The method is most effective for treatment of disorders involving epithelial tissue, particularly gastrointestinal epithelium (including oropharynx, esophagus, stomach, intestines and colon).

The method provides the previously described composition, a combination of therapeutically effective dosage of a selected amino acid, or a combination of amino acids, with an effective amount of carbohydrate carrier(s) which increase(s) aqueous solubility and cellular absorption of the amino acid or amino acids for administration to the epithelial tissue of the patient.

The invention is particularly useful for delivery of therapeutic levels of amino acids which exhibit limited aqueous solubility, such as the dietary amino acids tryptophan, tyrosine, glutamine, aspartic acid, asparagine, glutamic acid, histidine, isoleucine, leucine, methionine, and phenylalanine. Both D- and L-amino acids, as well as amino acids such as citrulline, g-aminobutyric acid, hydroxyproline, and ornithine, for example, can be delivered by the method to increase cellular absorption.

Carbohydrate carriers useful for the composition administered in the method of the invention can be chosen from among the sugars, either monosaccharide or disaccharide, including, for example, D-allose, D-altrose, D-arabinose, D-erythrose, D-erythrulose, D-fructose, D-galactose, D-glucose, D-glyceraldehyde, D-gulose, D-lyxose, D-idose, D-mannose, D-psicose, D-ribose, D-ribulose, D-sorbose, D-tagatose, D-talose, D-threose, D-xylose, D-xylulose, maltose, lactose, and sucrose. In some patients or physiological conditions, as, for example, when it is important to choose a carbohydrate carrier which will not promote tooth decay or cause a sudden increase in blood glucose levels, it may be preferable to choose a polyol, or sugar alcohol, such as, for example, sorbitol, erythritol, maltitol, mannitol, or xylitol.

For children, particularly, a sugar alcohol may be a preferable carrier, and can produce added benefit beyond the desired therapeutic effect on the target tissue. For example, xylitol reduces the growth of Streptococcus pneumoniae and has been shown to have a preventive effect against acute otitis media when incorporated into chewing gum for children. (Uhari, M., et al., Brit. Med. J. (1996) 313(7066): 1180–1184.) Use of xylitol as a carbohydrate carrier for glutamine in a chewing gum formulation used to treat damaged oral or esophageal epithelial tissue after chemotherapy or bone marrow transplant can, therefore, also provide a protective benefit against a pathogenic organism.

The method comprises identification of physiologic disorders for which amino acid supplementation is indicated. More particularly, it provides a method for delivering increased intracellular amino acid supplementation to patients who exhibit symptoms of a physiologic disorder for which amino acid supplementation may be of therapeutic value. Numerous physiologic disorders, or diseases, have been linked, for example, to defective amino acid metabolism or defective absorption. In many situations, it is desirable to deliver large intracellular concentrations of an amino acid. In most situations, it is also preferable to do so by administering a limited dose of the selected amino acid or amino acids. This has not previously been possible, however, since many amino acids exhibit limited aqueous solubility and intracellular absorption—and must therefore be administered in large doses to achieve a desired effect. Physiological conditions for which amino acids supplementation has been indicated, and for which the method of the present invention is therefore beneficial for increasing intracellular delivery of amino acid supplements, are described below. These examples are not intended to limit the use of the method described herein, but are presented as examples of the wide variety of physiologic disorders for which the method of the present invention will be useful.

Enhancing Amino Acid Absorption for the Treatment of Children and Adults with Short Bowel Syndrome Short bowel syndrome is associated with surgical resection of the large intestine, and results in decreased surface area for absorption. The tissue of the bowel is often irritated, with accompanying symptoms such as cramping and diarrhea. An amino-acid based complete infant formula has been demonstrated to be effective in improving feeding tolerance, eliminating the need for parenteral nutrition, and improving intestinal function in children with severe short bowel syndrome. (Bines, J., et al., J. Pediatr. Gastroenterol. Nutr. (1998) 26(2): 123–128.) The present invention provides a method for increasing absorption of amino acids, particularly those amino acids which exhibit limited aqueous solubility and cellular uptake (e.g., tryptophan, tyrosine, glutamine, aspartic acid, asparagine, glutamic acid, histidine, isoleucine, leucine, methionine, and phenylalanine), in both children and adults with short bowel syndrome. When used for the treatment of patients with short bowel syndrome, the combination of therapeutically effective concentrations of amino acids and an effective amount of carbohydrate carrier provide increased levels of cellular uptake of amino acids into the intestinal epithelium, thereby providing a greater benefit to the patient and decreasing the amounts of amino acids that must be administered in order to achieve satisfactory therapeutic levels.

The combination of amino acids and carbohydrate carrier can be administered by a variety of pharmaceutically acceptable routes, including tablets, caplets, or capsules coated for delivery to the intestines or colon, as well as enema solutions or suspensions. Therapeutic dosages can be determined by the patient's physician, taking into consideration the age, size, and nutritional status of the patient.

Enhancing Amino Acid Absorption in Dialysis Patients

Dialysis patients commonly exhibit malnutrition. However, supplementation with a mixture of 8 essential and 9 nonessential amino acids has been shown to improve both health and mood of dialysis patients. (Mastroiacovo, P., et al., Clin. Ther. (1993) 15(4): 698–704.) In the method of the present invention, a combination of amino acids, in therapeutically effective amounts, is combined with an effective amount of a carbohydrate carrier to enhance solubility and cellular uptake of the amino acids, thereby increasing the therapeutic effect of amino acid supplementation and decreasing the dosage of amino acid required to achieve therapeutic effect.

A preferred mode of administration for dialysis patients is an enteric coated capsule, caplet, tablet, or coated bead containing a therapeutically effective amount of each of a variety of amino acids in combination with an effective amount of a carbohydrate carrier, such as sucrose or a polyol such as xylitol or sorbitol. For administration to diabetic patients, the preferred carbohydrate carrier is a polyol.

Enhanced Absorption of Glutamine for the Treatment of Wounds

Glutamine is precursor for the synthesis of nucleotides. It is both an activator of protein synthesis, and an inhibitor of protein degradation. It is an activator of glycogen synthesis, as well as a metabolic substrate for rapidly dividing cells. It is also an energy source for epithelial cells. Treatment of wounds, whether superficial or non-superficial, with the composition described for enhancing amino acid absorption, increases the absorption of glutamine into epithelial tissues, promoting more rapid wound healing. In addition to promoting wound healing by increasing glutamine absorption, however, the method provides a treatment which protects the wound from infection with pathogenic organisms. Filling infected wounds with sugar has been a practice for centuries. Honey has long been known to have antibacterial properties, due, in part, to the hypertonic sugar concentration. (Basson, N. et al., J. Dent. Assoc. S. Afr. (1994) 49(7): 339–341; Jeddar, A., et al., S. Afr. Med. J. (1985) 67(7): 257–258; Willix, D., et al., J. Appl. Bacteriol. (1992) 73(5): 388–394.)

A combination of sugar and povidone-iodine has been effective in promoting rapid healing, reducing bacterial contamination, and filling of defects with granulation tissue when used to treat patients for wounds, burns, and ulcers. (Knutson, R., et al., South Med. J. (1981) 74(11: 1329–1335.) However, while adding to the antibacterial properties of the hypertonic sugar environment, povidone-iodine kills white blood cells.

Combining glutamine with a carbohydrate carrier, therefore, provides a dual benefit for wound care: the increased glutamine absorbed by the epithelial cells provides an energy source for the epithelial cells, promoting cell division and healing, while also providing an energy source for the white blood cells needed to protect the underlying tissues from bacterial invasion, and the carbohydrate carrier protects the surface of the wound from bacterial contamination by providing an environment in which the high osmotic pressure and low water availability prevents microbial growth.

For wound care, the combination of a therapeutically effective amount of glutamine and a carbohydrate carrier, preferably sucrose or honey, is applied topically as a semi-solid formulation of a high concentration of sugar mixed with water and glutamine. Alternately, the combination is provided as a thick syrup for topical application to the affected area. Another alternative method of application is to provide the formulation as a solid to be applied to the wound area, drawing its aqueous fraction from the wound environment. Such a preparation, if provided in powdered or crystalline form, can be easily placed in a first-aid kit or other emergency care kit for wound treatment.

The combination can be especially effective for the treatment of burns, where the primary goals of treatment are protection of the tissue from infection and rapid regeneration of new tissue.

Enhancing Glutamine Absorption for the Treatment of Mucositis and Stomatitis

Mucositis is an inflammatory reaction, characterized by burn-like lesions or ulcerative lesions of the epithelial tissue of the gastrointestinal tract from mouth to anus. It may result from exposure to either ionizing radiation or chemotherapeutic agents. Stomatitis is any inflammatory reaction affecting the oral mucosa, with or without accompanying ulceration. Mucositis, particularly, is often further complicated by infection of the ulcerative tissue.

Studies have previously shown that oral application of glutamine solutions can improve the symptoms accompanying mucositis in some bone marrow transplant patients and chemotherapy patients. (Skubitz, K., and P. Anderson, J. Lab. Clin. Med. (1996) 127(2): 223–228; Anderson, P., et al., Bone Marrow Transplant (1998) 22(4): 339–344; Anderson, P., et al., Cancer (1998) 83(7): 1433–1439; U.S. Pat. No. 5,545,668 (Skubitz, et al., Aug. 13, 1996); and U.S. Pat. No. 5,438,075 (Skubitz, et al., Aug. 1, 1995.) Using the composition and method described herein, increased and effective intracellular glutamine concentrations can be delivered to epithelial tissues of the gastrointestinal system for the treatment of mucositis or stomatitis without increasing the absolute glutamine dosage.

In the method of the invention, the composition can be provided, for example, as a mouthwash, swish and swallow preparation, lozenge, or hard candy for treatment of oral ulcerations. For esophageal ulcers, a drink, including a sugared drink, a milkshake, or a frozen slurry can be used. Biodegradable inserts can also be used to treat the mouth and throat. Children, as well as adults, with mucositis or stomatitis can be treated using any of these preparations, but may prefer a preparation of carbohydrate, glutamine, and flavorings delivered as a popsicle or in combination with sherbet, an ice, or ice cream. These methods of delivery provide the added benefit of soothing cold on the ulcerative tissue. A chewing gum preparation, preferably a chewing gum with a semi-solid or liquid center, can also be used for the treatment of oral and esophageal ulcers.

For gastric ulcer therapy, tablets, capsules, capsules, or coated beads containing the carbohydrate/glutamine composition can be administered. For intestinal ulcerations, coated tablets, caplets, capsules, or coated beads can be administered for either enteric or colonic delivery. Methods for providing enteric coatings or coatings for colonic delivery are known in the art and have been described previously herein.

Enhancement of Glutamine Absorption for the Treatment of Cryptosporidiosis

*Cryptosporidium parvum* is a leading cause of persistent diarrhea in developing countries. Due to its resistance to chlorine, it has also become a threat in some United States water supplies. Cryptosporidiosis is particularly problematic in AIDS patients, the elderly, and the very young, in whom it causes a severe, life-threatening diarrhea. *Cryptosporidium parvum* infects the intestinal tissue, but does not infect beyond the most superficial surface of the intestinal epithelium. In a piglet model, approximately two-thirds of the intestinal villus surface area was damaged during *Cryptosporidia* infection. In the remaining epithelial tissue, increased glutamine metabolism is associated with a sodium-hydrogen exchange coupled to a chloride transport mechanism. Because of its direct association with the chloride transport mechanism, glutamine can be particularly therapeutic for repair of tissue damaged by *Cryptosporidium* infection. (Guerrant, R., *Emerging Infectious Diseases* (1997) 3(1): 51–57.) Infected tissue has lost much of the absorptive surface area, however, and the method of the present invention, by treating the patient with the composition of carbohydrate carrier and a therapeutic dose of glutamine, enhances glutamine uptake in the remaining cells to compensate for the decreased absorptive surface area.

The composition can be administered using a coated capsule, tablet, or caplet for intestinal delivery. Alternately, the composition can be infused or administered as an enema solution to coat the intestinal lining with the glutamine/carbohydrate carrier and enhance glutamine absorption into the remaining intestinal epithelial cells.

The method can also be useful as a factor in disease prevention, since glutamine is known to provide a primary energy source for white blood cells, which migrate among the cells of the intestinal lining and are responsible for destruction of pathogenic organisms such as *C. parvum*. Enhancement of glutamine absorption into the epithelial and white blood cells by the method of the present invention therefore provides a method for improving the immune response while maintaining the structural integrity of the epithelial lining of the intestine. For patients at risk for *Cryptosporidium* infection, enteric-coated capsules can be administered to maintain epithelial cell integrity and improve the immune response.

Enhancement of Glutamine Absorption to Improve Post-Surgical Wound Healing in the Gastrointestinal Tract Following surgical resection within the oral cavity, the intestine, or bowel, epithelial tissue damage can be treated by the method of the present invention to increase tissue integrity and promote wound healing. Following oral surgery, a swish and swallow preparation, mouthwash, lozenge, candy, or chewing gum preparation containing the composition of the present invention can be provided to the patient to allow easy administration of a therapeutically effective dose of glutamine in combination with a carbohydrate carrier. Particularly in patients who have undergone oral surgery, non-cariogenic carbohydrate carriers are preferred. Such sugar carriers include, for example, maltitol, lactitol, sorbitol, and xylitol. The most preferable polyol carbohydrate carrier for incorporation into the composition is xylitol.

Following intestinal surgery, the composition can be administered in the form of a coated tablet, caplet, capsule, or coated bead. The tablet, caplet, capsule, or coated bead can be coated with an organic solvent, such as, for example, cellulose acetate phthalate, cellulose acetate trimellitate, cellulose acetate succinate, hydroxypropyl methyl cellulose phthalate, hydroxypropyl methyl cellulose acetate succinate, and carboxy methyl ethyl cellulose, for enteric delivery. A tablet, caplet, or capsule can be coated with an acrylic-based resin to dissolve at higher pH (pH 7) to provide delivery to the distal ileum and colon. Alternatively, delivery of the glutamine/carbohydrate carrier composition can be provided in the form of a suppository, using a base such as cocoa butter or other glyceride, or as a rectal tablet without a conventional suppository base. Such compositions for suppository use have been described by Mizuno, et al., in U.S. Pat. No. 4,462,984, and Harwood, et al., in U.S. Pat. No. 4,439,194.

For treatment of diabetic patients, xylitol is the preferred carbohydrate carrier, as sorbitol is not absorbed in the intestine and could cause added intestinal discomfort.

Enhancement of Glutamine Absorption for Treatment of Low Birth Weight Infants

Neu, et al., have reported that very-low-birth-weight neonates who receive enteral glutamine supplementation have an increased survival rate. (J. Pediatrics, (1997) 131(5): 691–699.) The method of the present invention provides increased therapeutic intracellular glutamine dosages with decreased actual glutamine administration. In low-birth-weight neonates, particularly, achievement of the desired effect with smaller doses of nutrient can be essential.

For delivery of the composition, an enteral feeding tube is preferred. Any one of a number of carbohydrate carriers can be chosen, although sucrose and high fructose corn syrup are preferred. The therapeutic dosage of glutamine can be determined by the individual physician, using standard means of dosage calculation, bearing in mind that glutamine absorption is enhanced by combination with the carbohydrate carrier to levels of at least ten times higher than that achieved by administration of glutamine alone. Excipients can be added to the feeding formula, including flavorings and stabilizers. Added nutrients can also be included, including vitamins, amino acids, and recommended nutrients such as lactoferrin.

Enhancement of Glutamine Absorption to Treat Dermatological Lesions of Viral and Bacterial Origin A number of viral illnesses can be recognized by epithelial lesions. Among these are, for example, herpetic lesions around the mouth, the lesions associated with impetigo, and the painful lesions known as shingles, characteristic of varicella-zoster virus. The method of the present invention can be used to treat such lesions by topically applying the glutamine/carbohydrate carrier composition to the affected area. The glutamine component of the composition aids in healing by providing energy to the epithelial cells, while the sugar provides antibacterial properties to protect the damaged or infected tissue from further infection.

For topical application, a lotion or cream is preferred, incorporating glutamine, a carbohydrate carrier, and excipients such as stabilizing agents, gelling agents, or thickening agents.

Enhancement of Glutamine Absorption to Treat Patients Infected with Human Immunodeficiency Virus Gastrointestinal lymphoid tissue harbors more than 90% of the total lymphocytes in the body. Studies have shown that the gastrointestinal epithelium contains a large population of $CD34^+$ CD4-progenitors. (Mattapallil, J., et al., *J.*

*Virol.* (1999) 73(5): 4518–4523.) The gastrointestinal tract has also been demonstrated to be a major site of CD4$^+$ T cell depletion and viral replication in simian immunodeficiency virus infection. Other studies have shown that glutamine enhances production of T lymphocyte-derived cytokines. (Yaqoob, P. and P. Calder, *Cytokine* (1998) 10(10): 790–794.) Enhancing glutamine absorption into the intestinal mucosa by the method of the present invention therefore can provide a therapeutic benefit to HIV-infected patients, particularly those patients who are in the early stages of infection. Enhancement of the cytokine response to the viral infection can contribute to viral destruction by the immune system at the site of significant viral replication.

The glutamine/carbohydrate carrier composition can be administered in the form of an enteric-coated tablet, caplet, capsule, or coated bead. Suitable sugar carriers will preferably include, for example, sucrose, glucose, high fructose corn syrup, and xylitol.

Daily administration of recommended dietary levels of glutamine is preferred, since administration of this quantity of glutamine by the method of the present invention can result in an increased delivery of glutamine to the intestinal epithelium by a factor of, for example, 10–30×. Therefore, administration of more moderate amounts can produce an even greater intracellular concentration of glutamine than has been previously been achieved by administration of higher dosages of glutamine alone.

Enhancement of Glutamine Absorption for Cancer Therapy

Glutamine supplementation can be beneficial for cancer therapy for both its direct and indirect results. Glutamine supplementation has been shown to increase glutathione release from the gut in Fisher-344 rats. (Cao, Y., et al., *J. Parenter. Enteral Nutr.* (1998) 22(4): 224–227.) When given in conjunction with either radiation or chemotherapy, glutamine has been demonstrated to increase selectivity of either therapy for tumor cells. (Klimberg, V. and J. McClellan, *Am. J. Surg.* (1996) 172(5): 418–424.) In one study, tumor growth in rats receiving glutamine, either by gavage or as a food additive, decreased by 40% within three weeks. (Fahr, M., et al., *J. Parenter. Enteral Nutr.* (1994) 18(6): 471–476.) In a separate study, tumor volume loss in rats receiving methotrexate was nearly doubled when glutamine was added to the diet. (Klimberg, V., et al., *J. Parenter. Enteral Nutr.* (1992) 16 (6 Suppl): 83S–87S.) Decreased tumor growth in glutamine-supplemented rats has been correlated with greater natural killer cell activity, presumably due to glutathione-mediated suppression of prostaglandin E2 (PGE2) synthesis. (Klimberg, V., et al., *J. Surg. Res.* (1996) 63(1): 293–297.)

By providing normal cells with an energy source and a means to accomplish cellular repair, glutamine supplementation has also been indirectly associated with increased tolerance to chemotherapeutic agents.

The composition and method of the present invention provide increased glutamine absorption into gastrointestinal epithelial cells. Once absorbed into these cells, more glutamine is made available to circulate to other tissues of the body. Enhancement of absorption of glutamine also provides a means to increase glutathione production in the intestine. Cancer therapy can therefore consist of, or be enhanced by, daily administration of glutamine in admixture with an amount of carbohydrate carrier, such as, for example, sucrose, glucose, xylose, xylitol, high fructose corn syrup or corn syrup solids effective to increase glutamine absorption into the gastrointestinal epithelium. The composition and method can be used for both human and veterinary cancer therapy.

Daily doses of glutamine will be determined by the individual patient's physician, taking into consideration factors which are known by those of skill in the art to affect dosage calculation, such as, for example, body size and age. Recommended daily doses of glutamine for cancer therapy are preferably at least at the maximum dietary intake of 3–4 grams per day, although lower doses can be administered, since the composition and method of the present invention increase glutamine absorption by at least a factor of ten, and more preferably, 100.

Other Uses for a Method for Increased Amino Acid Absorption

Although the method for treating physiological disorders in patients has been described primarily in terms of administration of glutamine, the invention is not intended to be limited to a method of administering enhanced levels of glutamine alone. For example, D-serine has been demonstrated to be therapeutic for the treatment of schizophrenia when administered in conjunction with antipsychotic medications. (Tsai, G., et al., *Biol. Psychiatry* (1998) 44(11): 1081–1089.) Enhanced absorption of D-serine into the intestinal epithelia after oral administration, can, therefore, provide a method for increasing available D-serine for systemic circulation. Canavan disease, an autosomal genetic disorder, is proposed to benefit from supplementation of dietary aspartic acid. (Baslow, M. And T. Resnik, *J. Mol. Neurosci.* (1997) 9(2): 109–125.) Early detection of the disease, therefore, can be accompanied by aspartic acid supplementation by the method of the present invention to enhance uptake of aspartic acid, an amino acid with an aqueous solubility of only 0.778 g/100 g at 25° C., to protect against the progressive degeneration of the brain which is characteristic of the disease.

These are only two examples of a number of physiologic conditions which can be therapeutically treated using enhanced amino acid absorption provided by the method of the present invention. As amino acids are identified as having therapeutic value, dietary supplementation can be further enhanced by providing the amino acid supplement in combination with a carbohydrate carrier as described by the method of the invention.

Veterinary Use for Enhanced Amino Acid Absorption into Epithelial Cells

The early-weaned pig develops intestinal atrophy, and glutamine supplementation has been proposed to prevent intestinal epithelial damage and provide a benefit in swine production. (Wu, et al., J. Nutr. (1996) 126 (10): 2578–84.) The composition and method of the present invention can be used to enhance amino acid absorption into those epithelial tissue cells, thereby decreasing costs associated with amino acid supplementation. The composition and method are also useful for veterinary treatment of dogs and other mammals in whom chemotherapy has been initiated. For example, doxorubicin, associated with gastrointestinal ulcers in human chemotherapy patients, is the recommended treatment for a number of other mammalian cancers, including canine hemangiosarcoma. The composition and method of the present invention provide enhanced amino acid absorption into the damaged epithelium of the mammalian subject, as well as increasing systemically available amino acid by increasing absorption into the gastrointestinal epithelium.

Stable Glutamine Preparations for Administration to a Patient

The present invention also describes a composition for providing glutamine to a patient in a form which has improved aqueous solubility and stability. In one form, the composition can be provided as a granulated or powdered drink mix, contained in bulk packaging or packaged as individual doses. Before administration, the preparation can be constituted with water, juice, or other liquid to provide for easy administration and increase the absorption of glutamine into the epithelial tissue. Glutamine can also be provided in stable form with the sugar carrier as a solid solution in the form of a candy or lozenge. The patient can administer the glutamine/carbohydrate carrier composition by simply placing the candy or lozenge into his mouth and allowing it to remain there while the surrounding fluids dissolve it. In this aqueous environment, the carbohydrate can provide the carrier to facilitate absorption of the glutamine into the epithelial cells of the oral cavity, the esophagus, and the stomach.

Either the granulated/powdered formulation or the solid solution can also be administered to the environment of the small intestine or the large intestine by adding an enteric coating or an acrylic-based resin as previously described for delivery to the distal ileum or colon.

In any of these preparations, glutamine has a stable shelf-life and can be provided to the patient well in advance of the time of administration. The preparations can be stored in the clinic or the patient's home for administration as needed.

The invention is described with reference to various specific and preferred embodiments and techniques. However, it should be understood that many variations and modifications may be made while remaining within its scope.

All referenced publications, patents and patent documents are intended to be incorporated by reference, as though individually incorporated by reference.

What is claimed is:

1. A solid composition consisting essentially of a dry mixture of about 5–15% w/w glutamine;
   about 30–50 w/w % carbohydrate comprising an amount of a monosaccharide, a disaccharide or a combination thereof affective to enhance the cellular uptake of glutamine from aqueous solution;
   an effective amount of buffer or buffering agent; and about 1–5% w/w modified cellulose.

2. The composition of claim 1, wherein the glutamine is L-glutamine.

3. The composition of claim 1, wherein the carbohydrate comprises a disaccharide and a sugar alcohol or polyol.

4. The composition of claim 3, wherein the disaccharide is sucrose.

5. The composition of claim 3, wherein the sugar alcohol is sorbitol.

6. The composition of claim 1, wherein the buffering agent is anhydrous monobasic sodium phosphate.

7. The composition of claim 1 further comprising glycerin.

8. The composition of claim 7 further comprising a stabilizer, emulsifying agent, preservative, defoamant, flavoring, or a combination thereof.

9. The composition of claim 8, wherein the emulsifying agent comprises xanthan gum, carrageenan, or a combination thereof.

10. The composition of claim 8, wherein the preservative comprises methylparaben, potassium sorbate, or a combination thereof.

11. The composition of claim 8, wherein the defoamant comprises simethicone.

\* \* \* \* \*

UNITED STATES PATENT AND TRADEMARK OFFICE
CERTIFICATE OF CORRECTION

PATENT NO. : 7,041,651 B2
APPLICATION NO. : 10/796261
DATED : May 9, 2006
INVENTOR(S) : Petit, II et al.

It is certified that error appears in the above-identified patent and that said Letters Patent is hereby corrected as shown below:

On Title Page (item (75)), in "Inventors", in column 1, line 1, delete "Newtown," and insert - - Washington Crossing, - -, therefor.

column 2, lines 3-6, after "(1998) 22(4): 339-44.)" delete "Formulations for the administration of amino acids, particularly glutamine, are described in U.S. provisional patent application No. 60/134,442 filed May 17, 1999 and incorporated by reference herein." and insert the same on line 4 as a new paragraph.

column 22, line 6, in Claim 1, delete "affective" and insert - - effective - -, therefor.

column 22, line 35, in Claim 11, delete "defoamant" and insert - - defoament - -, therefor.

Signed and Sealed this

Twenty-second Day of August, 2006

JON W. DUDAS
*Director of the United States Patent and Trademark Office*